United States Patent
Reiserer et al.

(10) Patent No.: US 11,474,531 B2
(45) Date of Patent: Oct. 18, 2022

(54) ROBOTS AND ROBOTIC SYSTEMS FOR FLUID HANDLING AND TRANSPORT OF BIODEVICES AND APPLICATIONS OF SAME

(71) Applicant: VANDERBILT UNIVERSITY, Nashville, TN (US)

(72) Inventors: Ronald S. Reiserer, Nashville, TN (US); John P. Wikswo, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 17/578,779

(22) Filed: Jan. 19, 2022

(65) Prior Publication Data

US 2022/0229441 A1    Jul. 21, 2022

Related U.S. Application Data

(60) Provisional application No. 63/300,313, filed on Jan. 18, 2022, provisional application No. 63/163,160, filed on Mar. 19, 2021, provisional application No. 63/139,138, filed on Jan. 19, 2021.

(51) Int. Cl.
| | |
|---|---|
| *G05D 1/02* | (2020.01) |
| *G05D 1/08* | (2006.01) |
| *C12M 3/00* | (2006.01) |
| *B60L 53/12* | (2019.01) |
| *C12M 1/00* | (2006.01) |
| *C12M 1/36* | (2006.01) |
| *B60B 19/00* | (2006.01) |

(52) U.S. Cl.
CPC ............ *G05D 1/0225* (2013.01); *B60L 53/12* (2019.02); *C12M 23/44* (2013.01); *C12M 23/50* (2013.01); *C12M 23/52* (2013.01); *C12M 29/10* (2013.01); *C12M 41/48* (2013.01); *G05D 1/0291* (2013.01); *G05D 1/0891* (2013.01); *B60B 19/003* (2013.01)

(58) Field of Classification Search
CPC .. A01N 1/0247; A01N 1/0242; A01N 1/0284; A01N 1/0289; A61M 1/3666; A61M 25/06
See application file for complete search history.

(56) References Cited

U.S. PATENT DOCUMENTS

| | | | | |
|---|---|---|---|---|
| 2020/0348324 | A1* | 11/2020 | Wikholm | G01N 35/1072 |
| 2020/0377317 | A1* | 12/2020 | Zoghzoghy | B65G 43/10 |
| 2021/0222110 | A1* | 7/2021 | Blanchard | C12M 41/40 |

OTHER PUBLICATIONS

Albert P. Li. "Screening for human ADME/Tox drug properties in drug discovery" Drug Discovery Today. vol. 6, Issue 7, Apr. 1, 2001, pp. 357-366. (Year: 2001).*

* cited by examiner

*Primary Examiner* — Michael L Hobbs
(74) *Attorney, Agent, or Firm* — Locke Lord LLP; Tim Tingkang Xia, Esq.

(57) ABSTRACT

A robot for transporting a biodevice from one place to another place, comprising a body for carrying the biodevice; a driving assembly for driving the body in omnidirectional motion; a sensing unit for sensing at least a position and orientation of the body; and a control unit coupled to the driving assembly and the sensing unit for generating one or more control signals based on at least the sensed position and orientation of the body to drive the driving assembly so as to move the body to a desired place and to arrive with the correct orientation.

33 Claims, 46 Drawing Sheets

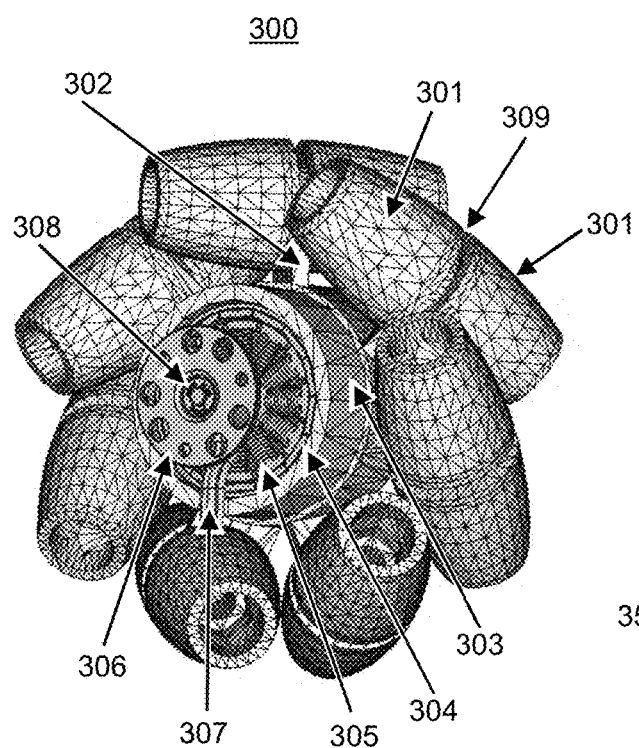
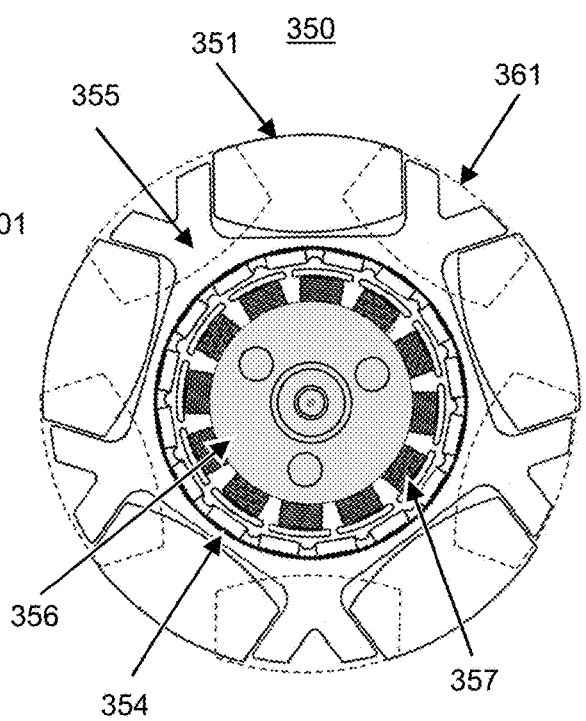
FIG. 3A
FIG. 3B

Step 1

Step 2

Step 3

Step 4

Step 6

Step 9

Step 11

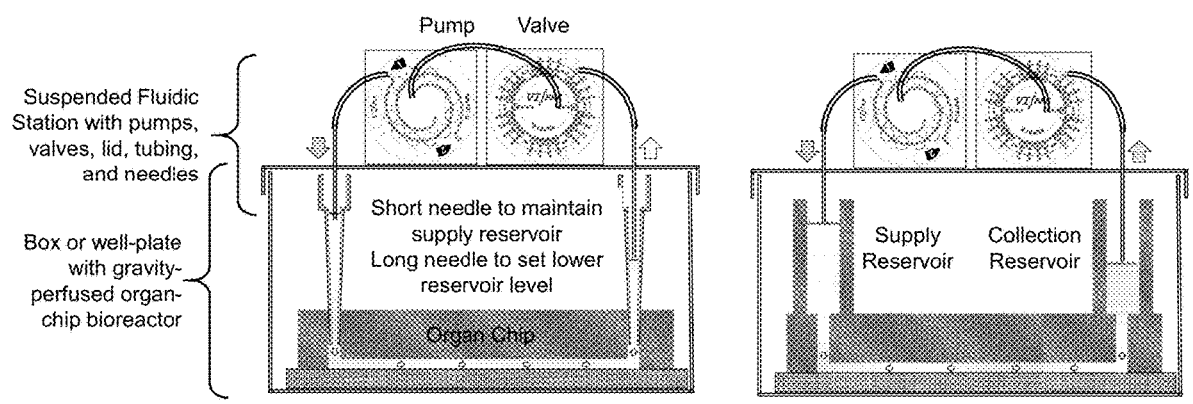
FIG. 20A
FIG. 20B
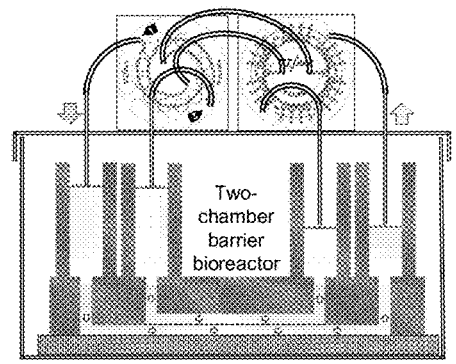
FIG. 20C
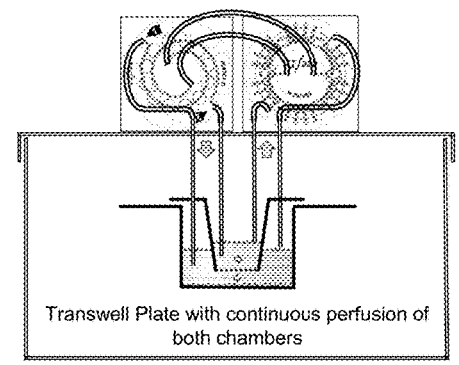
FIG. 20D

ROBOTS AND ROBOTIC SYSTEMS FOR FLUID HANDLING AND TRANSPORT OF BIODEVICES AND APPLICATIONS OF SAME

CROSS-REFERENCE TO RELATED PATENT APPLICATIONS

This application claims priority to and the benefit of U.S. Provisional Patent Application Ser. Nos. 63/139,138, filed Jan. 19, 2021, 63/163,160, filed Mar. 19, 2021, and 63/300, 313, filed Jan. 18, 2022, which are incorporated herein by reference in their entireties.

STATEMENT AS TO RIGHTS UNDER FEDERALLY-SPONSORED RESEARCH

This invention was made with government support under Grant No. UH3TR002097 awarded by the National Institutes of Health (NIH) National Center for Advancing Translational Sciences (NCATS), National Institute of Neurological Disorders and Stroke (NINDS), and Eunice Kennedy Shriver National Institute of Child Health and Human Development (NICHD); Grant No. U01TR002383, and (through Vanderbilt University Medical Center) UL1TR002243 awarded by NCATS; and by the National Science Foundation (NSF) under Grant No. 2117782. The government has certain rights in the invention.

FIELD OF THE INVENTION

The invention relates generally to autonomous robotic systems, and more particularly to robots and distributed robotic systems for fluid handling and transport of biodevices such as well plates, arrays of organ chips, and other biodevices, and applications of the same.

BACKGROUND OF THE INVENTION

One limitation of conventional well-plate robotics is that a limited number of plate-moving techniques become the workflow choke points between single-operation work stations such as incubators, fluid handlers, and plate readers. This can be acceptable in simple, synchronous, linear "load-expose-read" high-throughput screening for drug discovery workflows, which seldom have any in-process adjustments. However, this is not an optimum topology for a massively parallel, robot-scientist workflow where multiple operations should be performed in parallel and asynchronously using one or more copies of rate-limiting work stations.

Therefore, a heretofore unaddressed need exists in the art to address the aforementioned deficiencies and inadequacies.

SUMMARY OF THE INVENTION

One aspect of the present invention relates to a robot for transporting a biodevice from one place to another place. The robot in one embodiment comprises a body for carrying the biodevice; a driving assembly for driving the body in omnidirectional motion; a sensing unit for sensing at least a position and orientation of the body; and a control unit coupled to the driving assembly and the sensing unit for generating one or more control signals based on at least the sensed position and orientation of the body to drive the driving assembly so as to move the body to a desired place and arrive with the correct orientation and direction of approach.

In one embodiment, the driving assembly comprises a plurality of movable members coupled to the body, and a plurality of drivers engaged with the plurality of movable members for operably driving the plurality of movable members individually and/or cooperatively.

In one embodiment, each movable member comprises a holonomic wheel including a Mecanum wheel or an Omni wheel or a swivel drive.

In one embodiment, the sensing unit is configured to sense at least the position and orientation of the body using at least one of infrared light, visible light, ultrasonic waves, and electromagnetic waves or fields.

In one embodiment, the sensing unit comprises optical sensors, LiDAR sensors, accelerometers, gyroscopes, inertial measurement units (IMUs), magnetic proximity sensors, and/or pressure sensors.

In one embodiment, the control unit comprises a microcontroller for operating the driving assembly and the sensing unit, and wireless communication with external devices.

In one embodiment, the control unit further comprises a power supply circuit with capabilities for battery-free operation of the robot, or for battery-powered operation of the robot.

In one embodiment, the power supply circuit comprises at least one battery for the battery powered operation of the robot.

In one embodiment, the at least one battery is a rechargeable battery operably rechargeable with wired recharging or wireless recharging.

In one embodiment, the body comprises an object handling mechanism for carrying and loading the biodevice.

In one embodiment, the handling mechanism includes the ability to raise and lower the biodevice to interface with fluid-handling, docking, and transfer stations.

In one embodiment, the body further comprises a kinematic alignment fixture for ensuring that the robot or its cargo arrives at each location with specified accuracy.

In one embodiment, the robot is configured to operably adjust tilt of the biodevice being carried so that the tilt compensates for an inertial force associated with acceleration and ensures that a vector sum of gravity and inertial force are always perpendicular to a bottom of the biodevice to avoid sloshing or spilling of any fluid contents of the bioobject.

In one embodiment, the robot is configured to operably level the biodevice being carried as it ascends or descends a ramp between places.

In another aspect, the invention relates to a robotic system for fluid handling and transport of biodevices. The robotic system in one embodiment comprises a rack-type incubator having a plurality of decks, each deck having a plurality of stations, each station being configured to accommodate a perfusion module or a cell growth and plate inoculation module; and one or more robots, each robot being a holonomic robot configured to carry and load a biodevice to a desired module, wherein the rack-type incubator is configured such that two or more robots are simultaneously operable on a deck without interference.

In one embodiment, the robotic system further comprises a means for moving a robot between decks, wherein the means comprises an elevator, or a vertical climbing shaft having climbable walls with a closeable entry door.

In one embodiment, the robot is configured to operably climb up or down on the climbable walls, thereby moving between decks.

In one embodiment, the robotic system further comprises an external robot arm for delivering a mobile robot or a well plate to a delivery channel of the rack-type incubator that is in communication with the elevator.

In one embodiment, each deck is connected to a continuous circulation fluid bus and a power bus.

In one embodiment, each robot comprises a body for carrying the biodevice; a driving assembly for driving the body in omnidirectional motion; a sensing unit for sensing at least a position and orientation of the body; and a control unit coupled to the driving assembly and the sensing unit for generating one or more control signals based on at least the sensed position and orientation of the body to drive the driving assembly so as to move the body to a desired place and arrive with the correct orientation and direction of approach.

In one embodiment, the driving assembly comprises a plurality of movable members coupled to the body, and a plurality of drivers engaged with the plurality of movable members for operably driving the plurality of movable members individually and/or cooperatively.

In one embodiment, each movable member comprises a holonomic wheel including a Mecanum wheel or an Omni wheel or a swivel drive.

In one embodiment, the sensing unit is configured to sense at least the position and orientation of the body using at least one of infrared light, visible light, ultrasonic waves, and electromagnetic waves or fields.

In one embodiment, the sensing assembly comprises optical sensors, LiDAR sensors, accelerometers, gyroscopes, inertial measurement units (IMUs), magnetic proximity sensors, and/or pressure sensors.

In one embodiment, the control unit comprises a microcontroller for operating the driving assembly and the sensing unit, and wireless communication with external devices.

In one embodiment, the control unit further comprises a power supply circuit with capabilities for battery-free operation of the robot, or for battery- or supercapacitor-powered operation of the robot.

In one embodiment, the body comprises an object handling mechanism for carrying and loading the biodevice.

In one embodiment, the body further comprises a kinematic alignment fixture for ensuring that the robot arrives at each location with specified accuracy.

In one embodiment, the robot is configured to allow robotic exchange of one perfusion module for another.

In one embodiment, the robotic system is configured such that an HTS Transwell plate and a well plate beneath it can be separately captured.

In one embodiment, the biodevices comprise well plates, chemostats, organ chips, transwell-plates, or other fluidic reservoirs that are contained in a multi-element biodevice array.

In one embodiment, the one or more robots are operable either as a single unit or in combination as a swarm.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 3A-3B respectively show Mecanum and Omni wheels used, according to embodiments of the invention.

FIGS. 20A-20D show how CAPCAS can perfuse biodevices that are contained in boxes that are transported by the robot, according to embodiments of the invention.

DETAILED DESCRIPTION OF THE INVENTION

Figure 1:
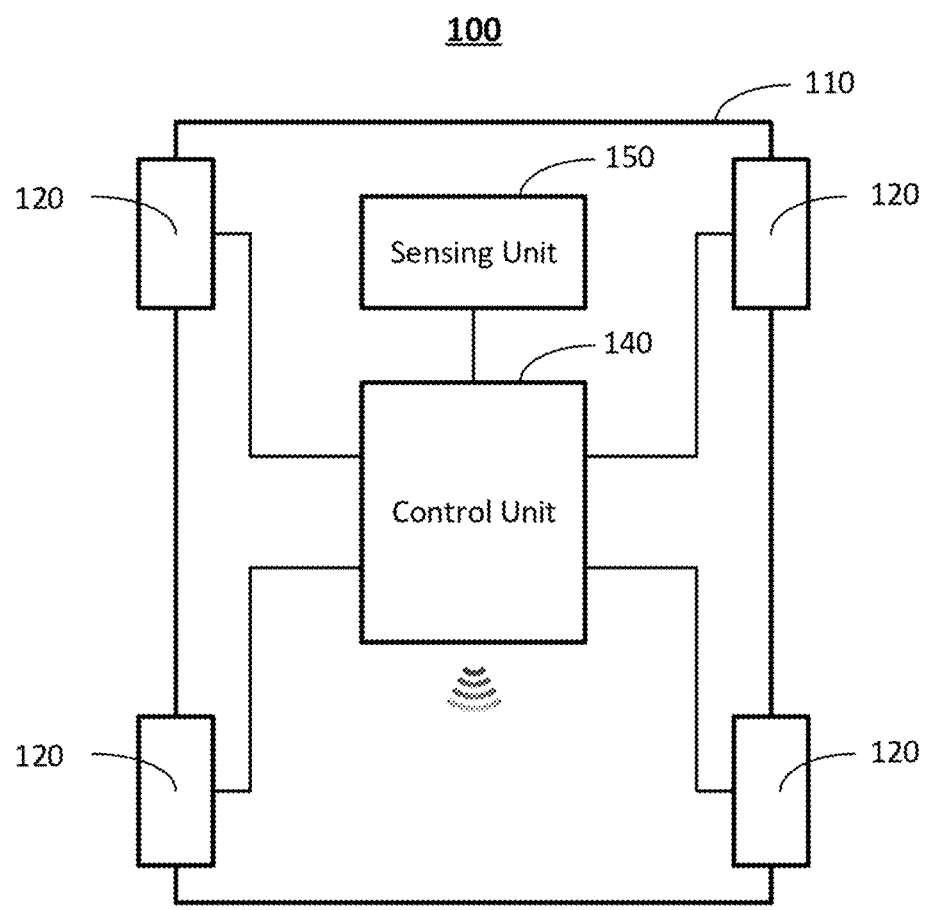
FIG. 1 shows schematically a block diagram of a robot according to embodiments of the invention.

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In light of the ongoing development of self-driving biological laboratories that can function as robot scientists that design, conduct, and analyze tens of thousands of experiments on hundreds to thousands of chemostats, bioreactors, well plates, and other biological systems, there is a pressing need to overcome the rate-limiting features of conventional high-throughput screening (HTS) systems and their fixed-location, rigid-arm robots. As an example, we will consider a Continuous Automated Perfusion Culture Analysis System (CAPCAS) that has within it multiple modules, each of which contains, in this exemplary case, a Multi-Well Chemostat with 48 independent chemostats with volumes of 1 to 2 milliliters. Because the CAPCAS utilizes a multi-well microformulator, each of the 48 wells in a Multi-Well Chemostat or bioreactor plate within the single multiwell perfusion module that supports its perfusion and analysis could be running a different experiment. Different modules in the same CAPCAS could be configured to run different types of biodevices, for example well plates in one module, chemostats in another, and organ chips in a third. The dozens of multi-well chemostat/biodevice perfusion modules in a single CAPCAS enclosure could be implementing a totally different protocol independent of the timing stage or configuration of other plates, and all protocols being evolved in real time in response to on-board sensors and machine learning. A full CAPCAS might have hundreds of these modules, which would be difficult to maintain and analyze using conventional HTS robotics. An iPlateBot could also be configured to allow robotic exchange of one perfusion module for another.

To support such a multi-threading robot-scientist environment, one objective of this invention is to develop a compact, autonomous, holonomic iPlateBot, a three- or four-wheeled plate-transporting robot, which is configured to move in arbitrary x-y directions on a CAPCAS deck, and lift a plate into a position beneath any of twelve fluidic interface stations, hereafter also termed fluidic stations, at which the fluidic interface assemblies are suspended so as to provide media formulation, perfusion, withdrawal, analysis and other functions to the bio-objects in each plate well, all guided by robot-scientist software. Computer controlled latches at the fluidic-interface station operably hold the plate once delivered, freeing the iPlateBot for another task. The WiFi-controlled microprocessors on the iPlateBot operably control the motor on each holonomic wheel so that the iPlateBot can, for example, enter from the front of a plate and depart from the side, allowing for a streamlined, self-organizing, and coordinated flow of multiple iPlateBots on a single deck. The advantage of having the iPlateBot attach the well plate or other biodevice to a suspended fluidic interface station is that after the plate is latched in place and the iPlateBot departs, the space beneath the plate is vacant, which enables random XY access to other plates suspended elsewhere above the deck, such that one of the many iPlateBot robots could reach any and all plates on a fluidic station above the deck without disturbing any already-suspended plates.

For navigation, the iPlateBot has a sensing assembly that is configured to sense at least the position and orientation of the body using at least one of infrared light, visible light, ultrasonic waves, and electromagnetic waves or fields. The sensing modalities could include optical sensors, LiDAR sensors, accelerometers, gyroscopes, inertial measurement units (IMUs), magnetic proximity sensors and/or pressure sensors.

The operation of the iPlateBot drive system, sensors, and other internal mechanisms and the interaction of the iPlateBot with other iPlateBots, elevators, or analytical instruments will be controlled by a combination of on-board microcontrollers, a WiFi-connected master control computer, and by wireless communication with external devices. The external devices can be, but are not limited to, smart devices including smart phones and tablets, computers, database servers and/or cloud servers. The external devices may have a graphic user interface (GUI) installed through which calibration and operation commands of the robot can be initiated, and the status of the robot can be visualized. The control unit also contains a power supply circuit with capabilities for battery-free operation of the robot, or for battery-powered operation of the robot. The power source could be a supercapacitor that is recharged automatically whenever an iPlateBot stops at a fluidic interface or docking station. The battery could be a rechargeable battery operably rechargeable with wired recharging or wireless recharging.

Different iPlateBots can be configured for specific functions. Since the iPlateBot can operate without the physical constraints of tracks or fixed arm geometry, optical sensors and kinematic alignment fixtures ensure that the iPlateBot arrives at each location with the required accuracy. The deck has a charging station to which an iPlateBot can return when necessary. As disclosed, two or more iPlateBots can service a deck without interference. The iPlateBots in effect provide swarm servicing of the CAPCAS Multi-Well Chemostats, bioreactors, perfused well plates, and organ chip arrays. Consumers now enjoy autonomous household vacuum robots, and iPlateBots provide the equivalent ease-of-use for plate handling, thereby breaking the economic and spatial bottlenecks posed by conventional laboratory automation. As the number of operational decks in a CAPCAS incubator enclosure or rack system is increased, additional iPlateBots and elevators can be used to move plates between decks. The iPlateBots represent a new class of holonomic plate-handling swarm robots that will allow the scale-up of the number of copies of perfused chemostats, bioreactors, and organ chips from 48 to thousands or more channels in a single, environmentally controlled bioenclosure such as an incubator or appropriately configured, instrumented, and sealed instrument rack.

The height of an iPlateBot is minimized so that it can move easily between the decks of a CAPCAS rack-type incubator that has a plurality of decks, each deck having a plurality of stations, each station being configured to accommodate a perfusion module or a cell growth and plate inoculation module. One or more holonomic iPlateBots are configured to carry and load a particular biodevice to a desired module, wherein the rack-type incubator is configured such that two or more robots are simultaneously operable on a deck without interference.

Specialized iPlateBots can provide other services within the multideck enclosure, including local UV sterilization, replacement of fluid-handling modules, delivery of a compact plate reader to any plate, delivery of a multi-motor well-stirring system, and delivery of reagent supply plates or reservoirs. The iPlateBot can deliver bulk media to fluid-handling stations, for example media that is stored in a small box that contains degassed media frozen in gas-impermeable bags, allowing fully automated media transport and delivery. We have shown that it is possible to create a box/bag system that has auto-sealing Luer locks such that a robot such as the iPlateBot or a robot arm could use a push-to-fit bag connector to deliver multiple bags with premixed contents to a fluidic control station. Small collection bags can hold 12 mL, and larger ones can hold 60 mL. This bag system could also provide sterilization solutions, such as strong acids or bases, or serve as wash or waste containers on each end of a valve system (e.g., the first and last port).

Because they are compact, low inertia, low traction, and low speed, the iPlateBots do not present an impact risk to humans, as do robot arms, so the iPlateBots can operate inside of a cell culture hood that is being used simultaneously by a human without endangering the human. Entrance and exit to the iPlateBot can either be through a bench-top-level portal in the back or side of the hood, or a simple elevator installed in the bench top connecting to a tunnel to another hood or multi-chemostat enclosure. Because of the low height of the iPlateBot, it can even enter or leave a hood by moving under the sash without having to raise the sash above the normal height that allows a human to insert a gloved forearm into the hood.

The iPlateBot is particularly useful in systems that require long-term perfusion of arrays of biodevices such as well plates, chemostats, organ chips, well plates, transwell-plates or other fluidic reservoirs that are contained in a multi-element biodevice array, in that the iPlateBot can deliver the array of biodevices to a perfusion system within a CAPCAS that is suspended above the working surface, termed a deck, upon which the iPlateBot operates. The iPlateBot can lift the biodevice array up to the perfusion system, the array can then be latched to the suspended perfusion system, and the iPlateBot can leave for another assignment. If the fluidic interface station contains fluid collection and withdrawal needles, these needles can be used to control the level of fluid in the supply and collection reservoirs of an organ chip or an array of organ chips.

The cargo for an iPlateBot can be a well plate, a box that contains one or more bioreactors or organ chips, a transwell plate containing cultured cells or zebrafish embryos, or items that might need to be transported with a CAPCAS or other biological laboratory work stations. In certain embodiments, the iPlateBot, the fluidic interface station, and the plate latching mechanisms could be configured to separately capture an HTS Transwell plate and the regular well plate beneath it. This would, for example, enable zebrafish embryos captured multiple Transwells in an HTS Transwell layer to be rapid transferred as a group into and then out of the plate beneath that contains the egg yolk proteins used to feed the embryos for a short interval of time.

The iPlateBots can be used in a variety of other ways, including moving well plates or disposable supplies such as boxes of pipette tips or empty well plates, between different locations in a single cell culture hood, or between distant work stations that are connected by an iPlateBot roadway. An iPlateBot can be configured to lift or lower bio-object arrays vertically, either to remove them from or place them on docking fixtures, raise them or lower them from a fluidic interface station that is suspended from above, or to remove or add a biodevice array from or to another iPlateBot. A mobile plate gripper at a fixed or moveable location can remove a biodevice array from an iPlateBot and place it on a stationary docking station for access by a fixed-arm robot, or to another iPlateBot for transport, for example if an iPlateBot stops functioning and it is necessary to recover the plate it was transporting.

Plate motion in most handling systems relies on large six degree-of-freedom (6 DOF) robots that are either stationary or mounted on rails or X-Y systems that are very large and require massive support structures. These robot systems have many restraints on reach, and access to plates often requires a special platform. Robots are very large in relationship to the plates and their range of motion. They also present a risk to human operators because of their speed and range of motion, actuator stiffness, and physical hardness, and hence humans are usually excluded from any space in which such a large robot is active.

The iPlateBot system utilizes a holonomic drive mechanism that allows plates to be moved between locations with limited infrastructure (a reasonably flat surface to run on). Robots may operate either as a single unit or in combination as a swarm to move many plates about a system without the large infrastructure of a typical robot system. This system also allows easy reconfiguration of the iPlateBot's locations and paths, which can allow the addition of new equipment into the system without requiring a position within the reach of a normal robot system.

The ability of the holonomic robot to move in any arbitrary direction in the X-Y plane or rotate around a Z axis is made possible by the use of either four independently motorized Mecanum wheels, three or four independently motorized Omni wheels, or a swivel or swerve drive with one or more motorized wheels whose axle orientation in the X-Y plane can be controlled by a separate actuator or motor. This ability is needed to ensure that the iPlateBot can approach a docking station with not only the correct location but also the correct orientation to properly interface with fixed features at that station, including perfusion needles, de-lidding latches, and perfusion needles.

The path between any two physical locations taken by an iPlateBot as it accomplishes an assigned workflow need not be fixed, but can be adjusted in real time in response to the current activities of other iPlateBots, such that interacting swarms of iPlateBots can be assigned various subtasks that are part of a complex task list.

The robots are capable of moving plates between sterile systems via a HEPA-filtered roadway system. This system can provide a path between biosafety cabinets and incubators which can lower the possibility of system contamination that can exist when humans handle plate transfers between system locations.

Integration with existing robot systems is important. iPlateBots can augment and extend existing systems by bringing plates within the reach of a standard plate-handling robot from remote locations while providing a safe operating interface between the human operators and larger HTS robots. One embodiment of the iPlateBot system allows plates to be picked up from flat surfaces. The iPlateBot can move to a location within the reach of the standard robot and then act as a picking platform for a standard robot system.

One iPlateBot can deliver a plate and another may take the plate to insert it in an analytical system. Utilizing multiple iPlateBots can speed up plate handling and sorting tasks.

Many open source robotics features like slow acceleration may be implemented to prevent spilling and sloshing in plates with large wells, e.g., 6 well plates or single well plates. The iPlateBot can do this, but can also adjust the tilt of the plate or biodevice array being carried by the iPlateBot so that the tilt compensates for the inertial force associated with the acceleration and ensures that the vector sum of gravity and inertial force are always perpendicular to the bottom of the well plate to avoid sloshing or spilling of any fluid contents of the bioobject. Similarly, the iPlateBot can level a plate as it ascends or descends a ramp between stations to ensure that the contents are not spilled.

When delivering a biodevice array to a fluidic interface station, an iPlateBot can stop at an adjacent station on the same deck of the CAPCAS unit, stop to de-lid the plate, and then deliver the de-lidded plate to its destination station.

iPlateBots have the capability of carrying specialized modules that can service plate locations with services such as spot sterilization with UV LEDs, imaging modules, and magnetic stirrers, as well as modules that can augment functionality of those plate locations, such as fluidic modules or plate-specific accessories.

Without intent to limit the scope of the invention, exemplary embodiments of the invention are illustrated in detail hereinafter with reference to accompanying drawings.

FIG. 1 shows one embodiment of the subject invention 100, termed an iPlateBot, and its constituent parts. The iPlateBot 100 has a body 110 for carrying a biodevice; a driving assembly 120 for driving the body 110 in omnidirectional motion; a sensing unit 150 for sensing at least the position and orientation of the body 110; and a control unit 140 coupled to the driving assembly 120 and the sensing unit 150 for generating one or more control signals based on at least the sensed position and orientation of the body 110 to drive the driving assembly 120 so as to move the body 110 to a desired place and arrive with the correct orientation. The biodevices include, but are not limited to, well plates, chemostats, organ chips, well plates, transwell-plates or other fluidic reservoirs that are contained in a multi-element biodevice array. In certain embodiments, the body 110 comprises an object handling mechanism for carrying and loading the biodevice. The handling mechanism includes the ability to raise and lower the biodevice to interface with fluid-handling, docking, and transfer stations. In certain embodiments, the driving assembly 120 comprises a plurality of movable members coupled to the body, and a plurality of drivers engaged with the plurality of movable members for operably driving the plurality of movable members individually and/or cooperatively. In certain embodiments, the driving assembly 120 includes holonomic drive mechanisms 120 that can be either Mecanum or Omni wheels or swivel wheels. The sensing unit 150 in certain embodiments is configured to measure relative and absolute location and orientation, acceleration, magnetic fields, tilt, pressure, and proximity to other objects. It can use laser (LiDAR) or ultrasonic ranging to determine proximity to other devices and fiducial markers, and utilize infrared light, visible light, ultrasonic waves, and electromagnetic waves or fields for detection and or communication with other iPlateBots or fiducial markers or docking stations. The control unit 140 operates all drive mechanisms and lifting mechanisms and maintains communication with command-and-control computers by wireless WiFi links.

Figure 2:
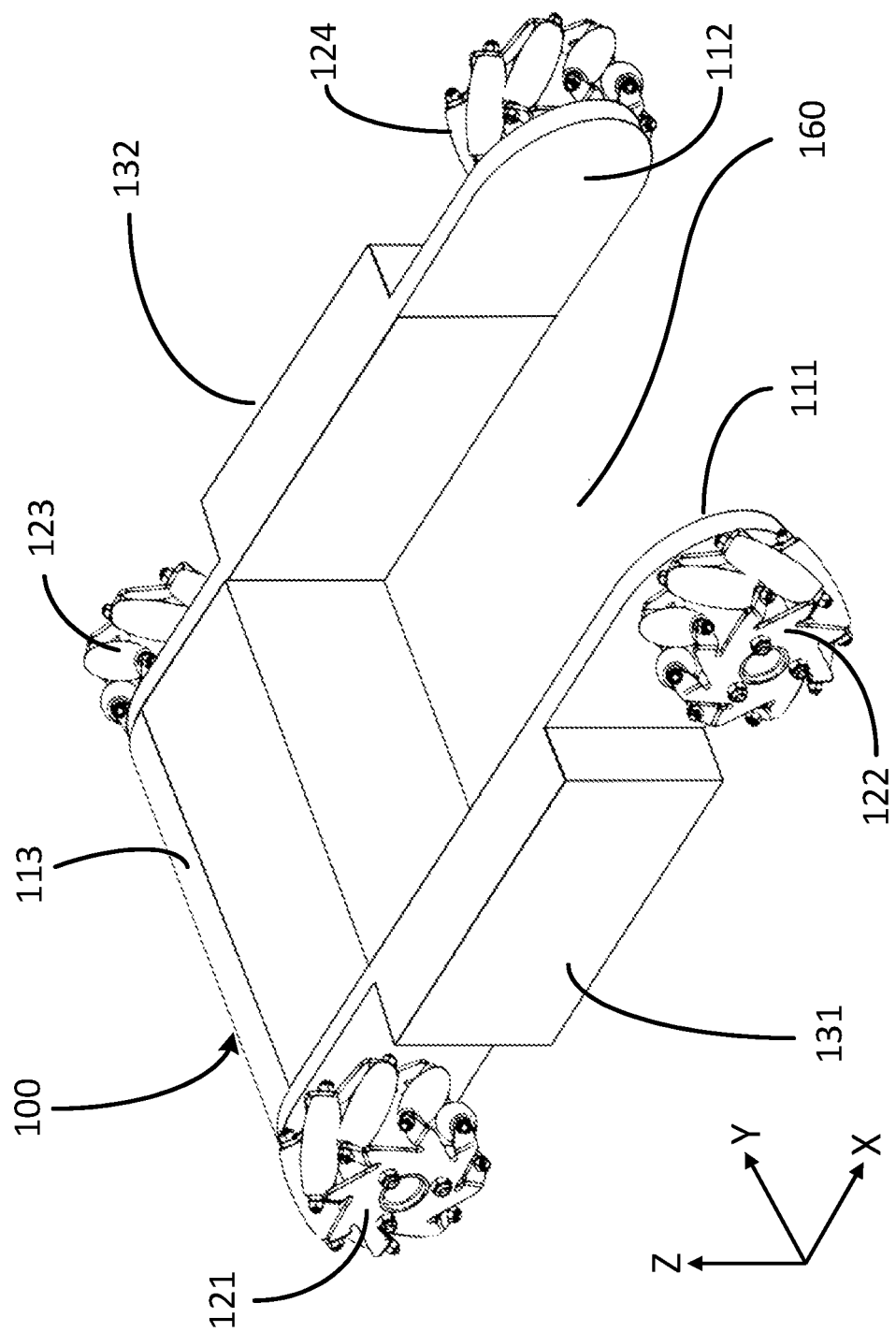
FIG. 2 shows a perspective view of one embodiment of the invention with a central opening to receive a well plate or another bio-object and the coordinate system used for describing this invention, according to embodiments of the invention.

FIG. 2 shows details of one embodiment of the iPlateBot 100. It has two left-handed Mecanum wheels 122 and 123, and two right-handed ones 121 and 124. If all wheels rotate in the same direction, the iPlateBot moves along the X axis, whereas if the right-handed wheels move in the opposite direction as the left-handed wheels, the iPlateBot moves along the Y axis. The relative angular velocities and direction of each wheel will determine the direction in the X-Y plane that the robot travels, or whether it rotates in place.

The ability to rotate in place is critical for the iPlateBot to arrive at a particular location with the correct orientation and direction of approach. The compartments 131 and 132 contain motor power and controls, and could also contain the motors if remote drives such as gear trains or chain or belt drives are used. Compartment 113 could house sensors, microcontrollers, and communications hardware. Because the motors do not occupy the central space of the robot, the central region 160 is available for capturing and transporting cargo. The side plates 111 and 112 provide mechanical support and can also provide gripper mechanisms (not shown) to grab the cargo in the space 160.

FIG. 3A shows one embodiment of a Mecanum wheel 300 with a brushless DC motor, which has a fixed flange 306 that supports a fixed armature 305 powered by four wires 307. The permanent magnets 304 are attached to the hub 303, which rotates around axle 308. The permanent magnets 304 are attached to the hub 303 while the fixed armature 305 is surrounded by but not fixed to the hub 303, but is attached instead to the fixed flange 306. The split rollers 301 are supported by struts 302 that are attached to the hub 303 and fit in the inter-roller gap 309, with the two roller parts 301 rotating around a shaft (not shown) attached to each strut. The important features of this wheel are that the hub 303 contains the motor, so that the central space 160 of the iPlateBot shown in FIG. 2 is clear to carry cargo, and the small wheel diameter that can be achieved with this design enables the construction of robots with a very low height that could pass freely within a 1 U vertical space. A Mecanum holonomic robot requires two right-handed motors and two left-handed ones, as shown in FIG. 2.

FIG. 3B shows an Omni wheel 350, with this embodiment having five rollers 351 on one layer and five others 361 on a second layer that is mechanically tied to the first but rotated by 36°, in this view hidden by the first layer. Again, the permanent magnets 354 are attached to the hub frame 355 and the armature 357 is attached to the flange 356.

Figure 4:
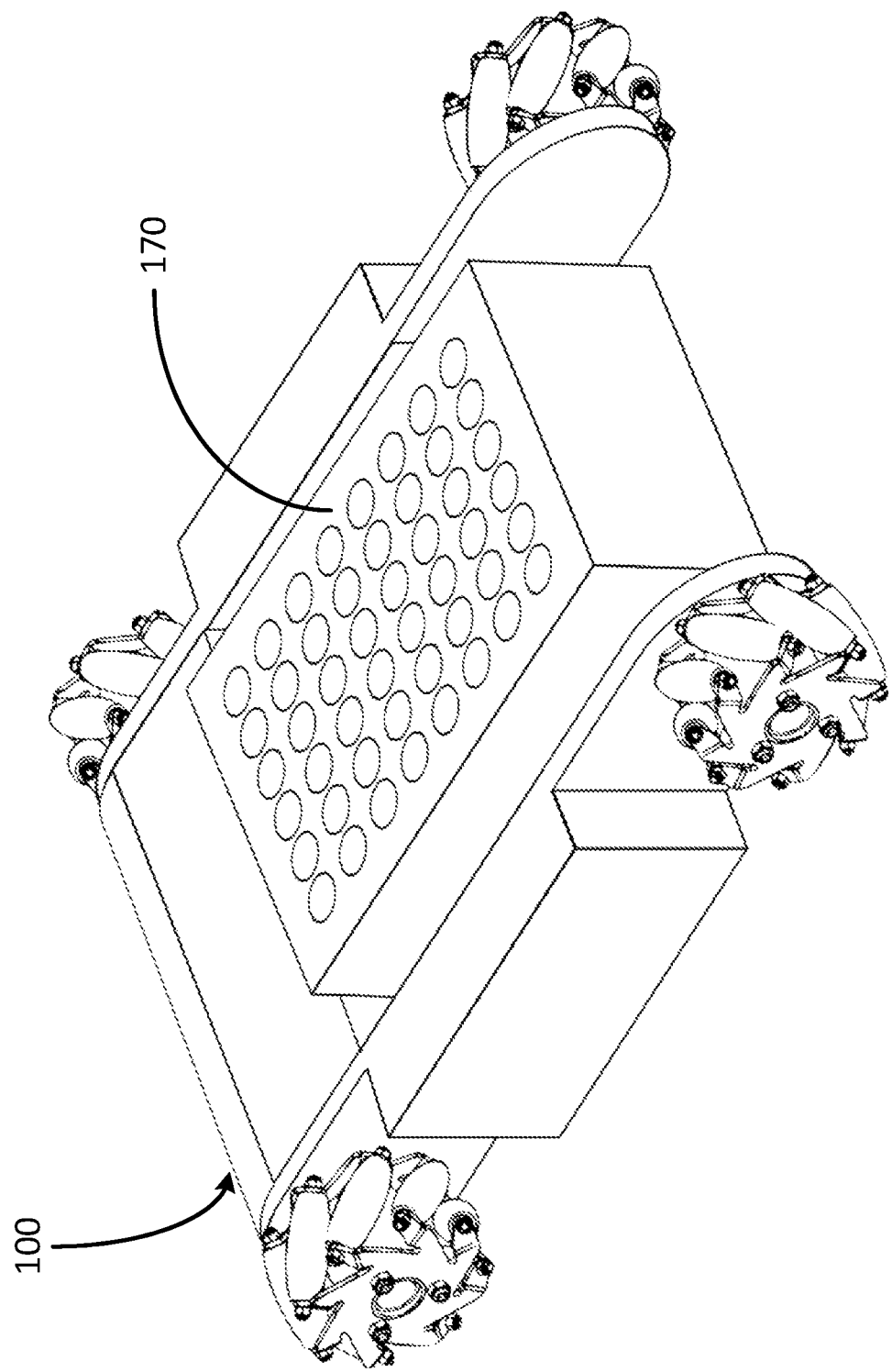
FIG. 4 shows a perspective view of one embodiment of the invention with a central opening holding a deep 48-well plate without a lid, according to embodiments of the invention.

FIG. 4 shows one embodiment of the iPlateBot 100 carrying a deep 48-well plate 170.

Figure 5:
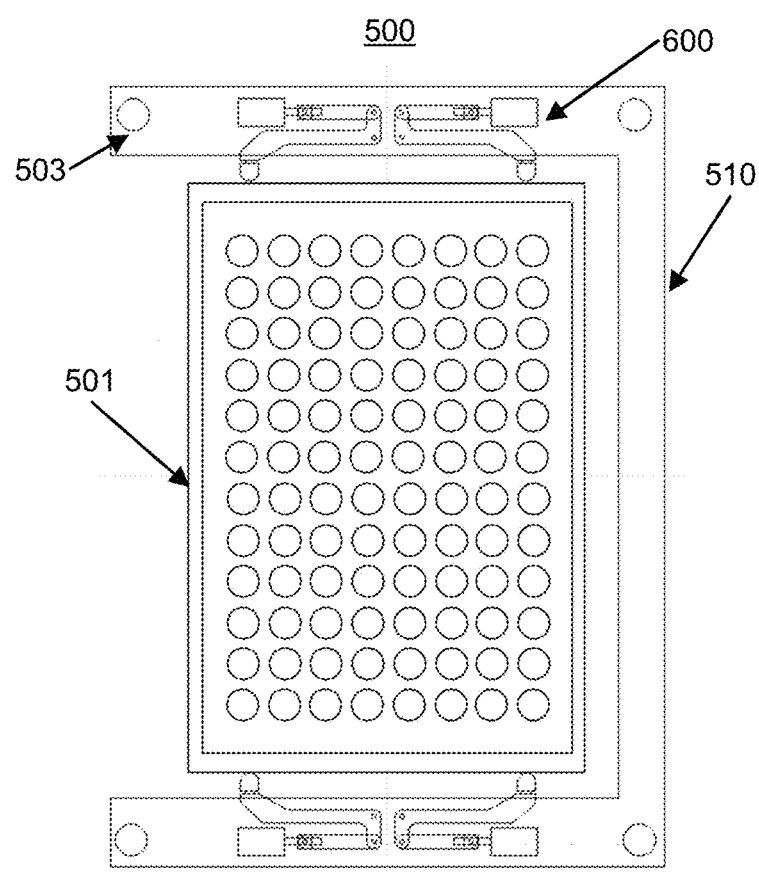
FIG. 5 shows a top view of one embodiment of the invention with four grippers holding a 96-well plate, according to embodiments of the invention.

FIG. 5 shows one embodiment of a robot 500 having gripper mechanisms 600 that can capture well plate 501. The frame 510 supports four gripper mechanisms 600. Holes 503 represent the location of motorized lifting screws (not shown) that can raise or lower the frame 510 to raise or lower the plate 501.

Figure 6:
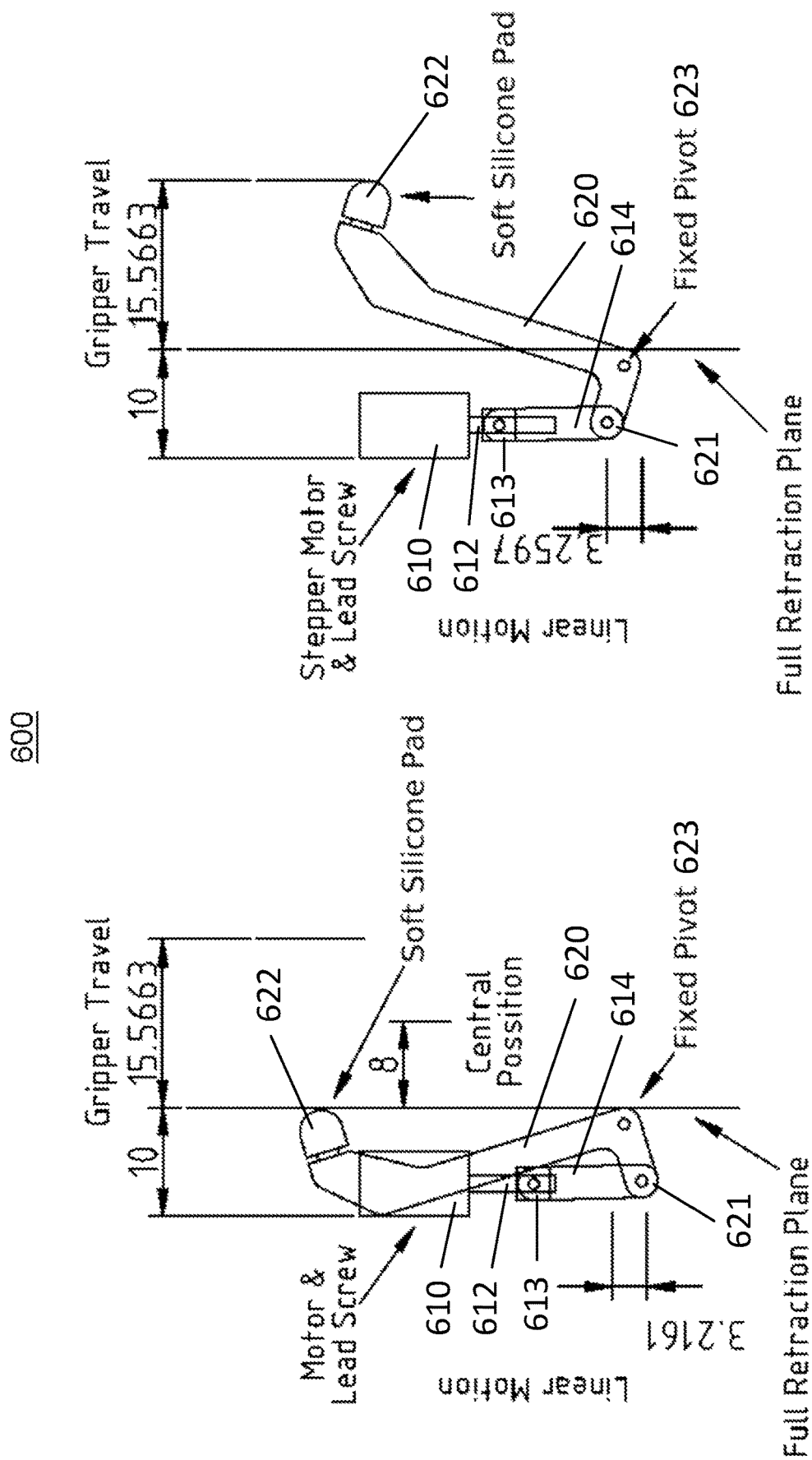
FIGS. 6A and 6B show details of one embodiment of the gripper mechanism and how it is actuated, according to embodiments of the invention.

FIGS. 6A and 6B provides construction and actuation details of one embodiment of a gripper mechanism 600. Rotation of the lead screw in one direction causes the gripper to retract (FIG. 6A) while rotation in the opposite direction causes it to extend (FIG. 6B). Specifically, as shown in FIGS. 5 and 6A-6B, the gripper mechanism 600 is coupled to the body frame 510 of the robot 500 and comprises a motor 610 and a gripper 620 coupled to the motor 610 through a lead screw assembly comprising the lead screw 612, a lead-screw nut 613, and a lead-screw linkage 614. The gripper 620 has a first end 621 pivotally coupled to the lead screw assembly 612, 613, 614 a second end 622 for capturing the well plate 501 (FIG. 5), and a fixed pivot 623 between the first end 621 and the second end 622. As such, when the motor 610 rotates in one direction to cause the lead screw assembly 612 and its linkage 614 to extend by driving the lead-screw nut 613 to the distal end of the of the lead screw 613 such that the linkage 614 pushes the first end 621 of the gripper 620 to move along an extended direction of the lead screw 612, meanwhile, the motion of the first end 621 along the extended direction of the lead screw 612 drives the second end 622 of the gripper 620 to retract, as shown in FIG. 6A, and when the motor 610 rotates in the opposite direction to cause the lead-screw nut 612 to retract towards the proximal end of the lead screw 612, which in turn causes the first end 621 of the gripper 620 to move along an retracted direction of the lead screw 612, the motion of the first end 621 along the retracted direction of the lead screw 612 results in the second end 622 of the gripper 620 to extend. The second end 622 of the gripper 620 can be in a fully retracted position (FIG. 6A), a fully extended position (FIG. 6B), or therebetween (FIG. 5). When in the fully retracted position, the second end 622 of the gripper 620 and the motor 610 are positioned within a same side of a full retraction plane, as shown in FIG. 6A. When a well plate 501 needs to be captured, the second end 622 of the gripper 620 is extended outside the full retraction plane to exert a desired lateral pressure on the well plate 501 so as to capture the well plate 501, as shown in FIG. 5. When the second end 622 of the gripper 620 is extended in the fully extended position (FIG. 6B), it may provide more pressure to the well plate 501. The second end 622 of the gripper 620 in one embodiment includes a soft silicone pad. The iPlateBot controller can monitor the motor current so that it can stop applying a voltage to the motor when the motor current rises to indicate that the gripper is either fully retracted, fully extended, or extended and delivering the desired pressure to the captured well plate or lid. A reverse polarity of the voltage can be applied to reverse the motion of the gripper.

Figure 7:
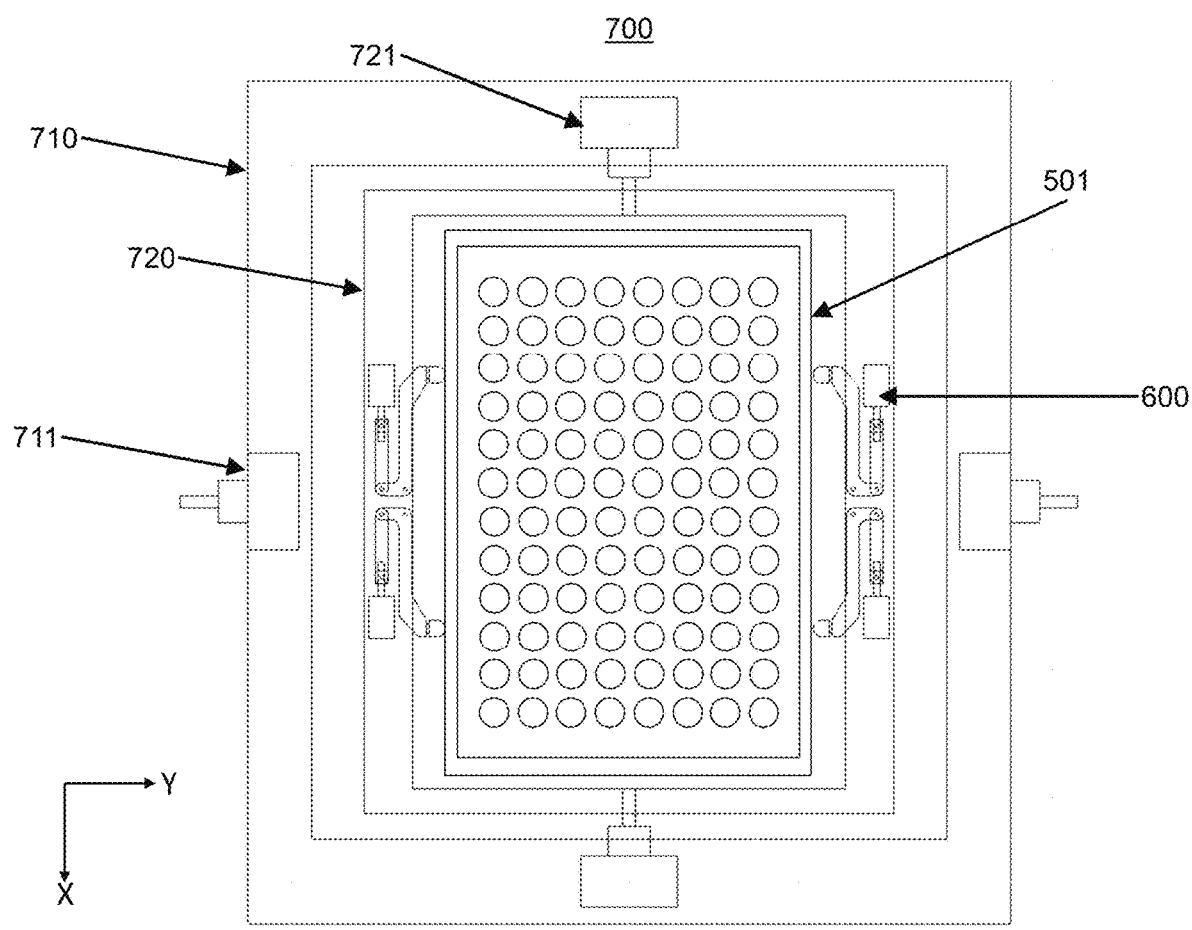
FIG. 7 shows a 96-well plate being held by four grippers inside a gimbal mount with two angular degrees of freedom to rotate the plate around the X or Y axes, according to embodiments of the invention.

FIG. 7 shows one embodiment of a robot 700 having a tilt mechanism with two degrees of freedom to adjust for deck or roadway tilt or accelerations or decelerations in any direction in the XY plane. The tilt of the outer frame 710 is determined by motor and axle assembly 711, which is attached to the body 710 of the robot 700, and supports rotations around the Y axis. The inner frame 720 and motor and axle 721 control rotations about the X axis. The inner frame 720 supports four gripper mechanisms 600 which capture well plate 501. The gimbal system could also be used to invert a well plate to empty its contents.

Figure 8:
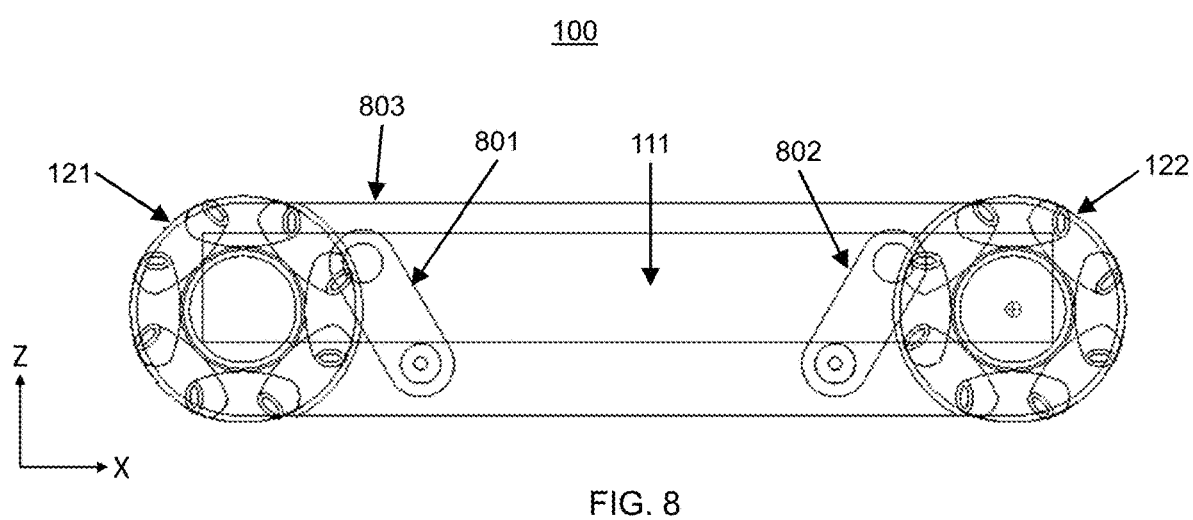
FIG. 8 shows a side view of the invention with details of Mecanum wheels and the plate-lifting mechanism, according to embodiments of the invention.

FIG. 8 shows a side view of the robot 100 shown in FIG. 2 with details of the lifting mechanism. There are two Mecanum wheels 121 and 122 of opposite handedness. Side plate 111 supports two independent lifting arms 801 and 802 that control the height of lifting surface 803. There are a multitude of methods by which 802 might be lifted, and the one shown here is for example only.

FIGS. 9A-9K show details of the iPlateBot holonomic robot in operation. Because the center of the iPlateBot is open, as shown in FIG. 2, has by design a low height, can engulf a well plate as shown in FIG. 4, and has a means to lift the plate vertically into an overhead fluid-handling station, the iPlateBot can drive up to the lid storage station, lift the lidded plate into a lid-retention mechanism such that the lid is latched in place, lower the de-lidded plate, move to an adjacent fluid-handling station, lift the plate into the plate-retention mechanism such that the plate is latched in place, lower its lifting mechanism, and depart that station for another assignment. The sequence can be summarized as drive in, store the lid, lower the plate, move the plate to a fluid-handling station, lift the plate, latch the plate, and leave. When the fluid-handing operations, such as a long chemostat or bioreactor run, are complete, an empty iPlateBot can return to the fluid-handling station, lower the plate, re-lid it, and take it to its next destination.

Figure 9A:
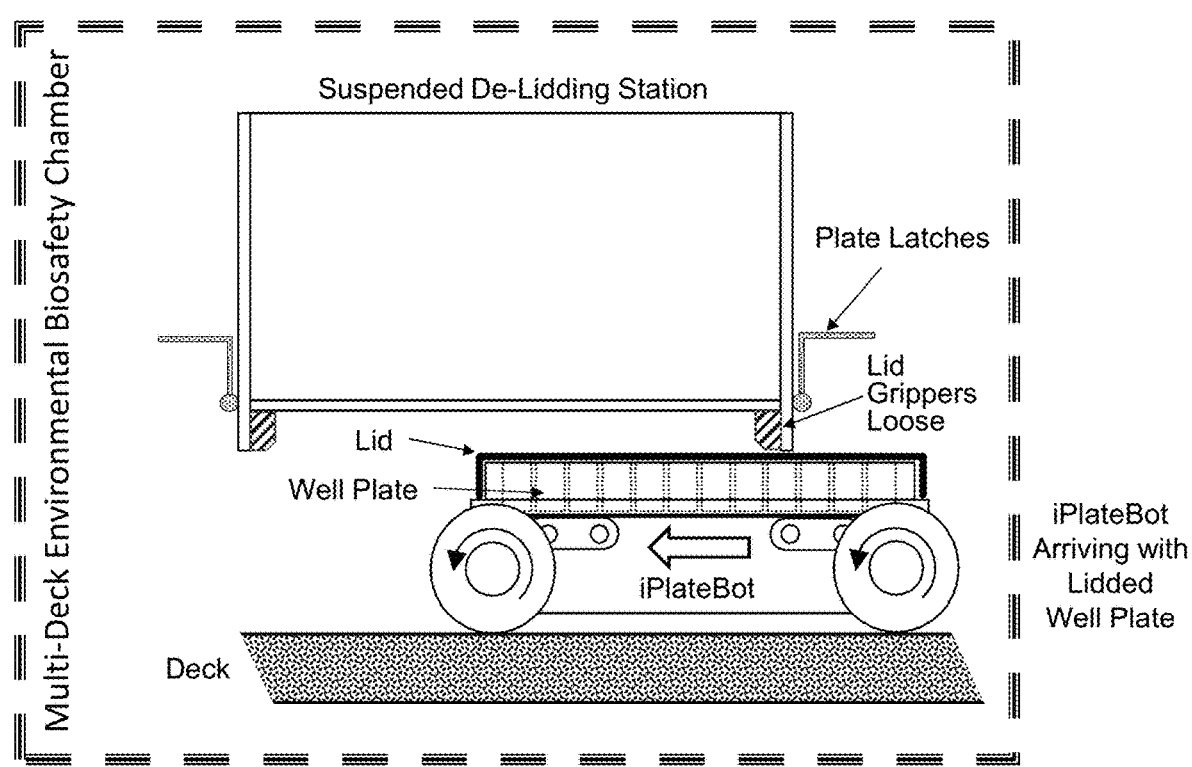
FIGS. 9A-9K show the invented robot through a sequence of delivering a lidded well plate to a de-lidding station, moving the de-lidded plate to a fluidic interface station, and the robot leveling a plate while moving up or down a ramp, or adjusting the tilt of a plate to compensate for inertial forces associated with lateral acceleration of the robot, according to embodiments of the invention.
Figure 9B:
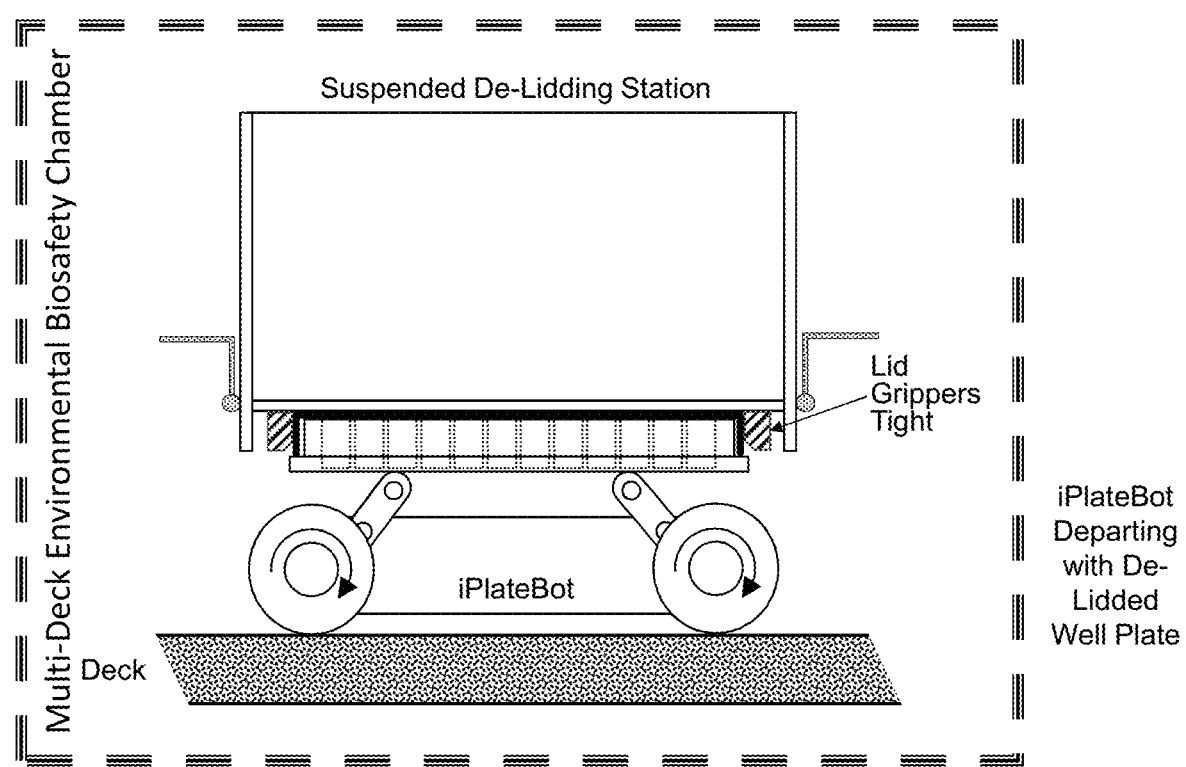
Figure 9C:
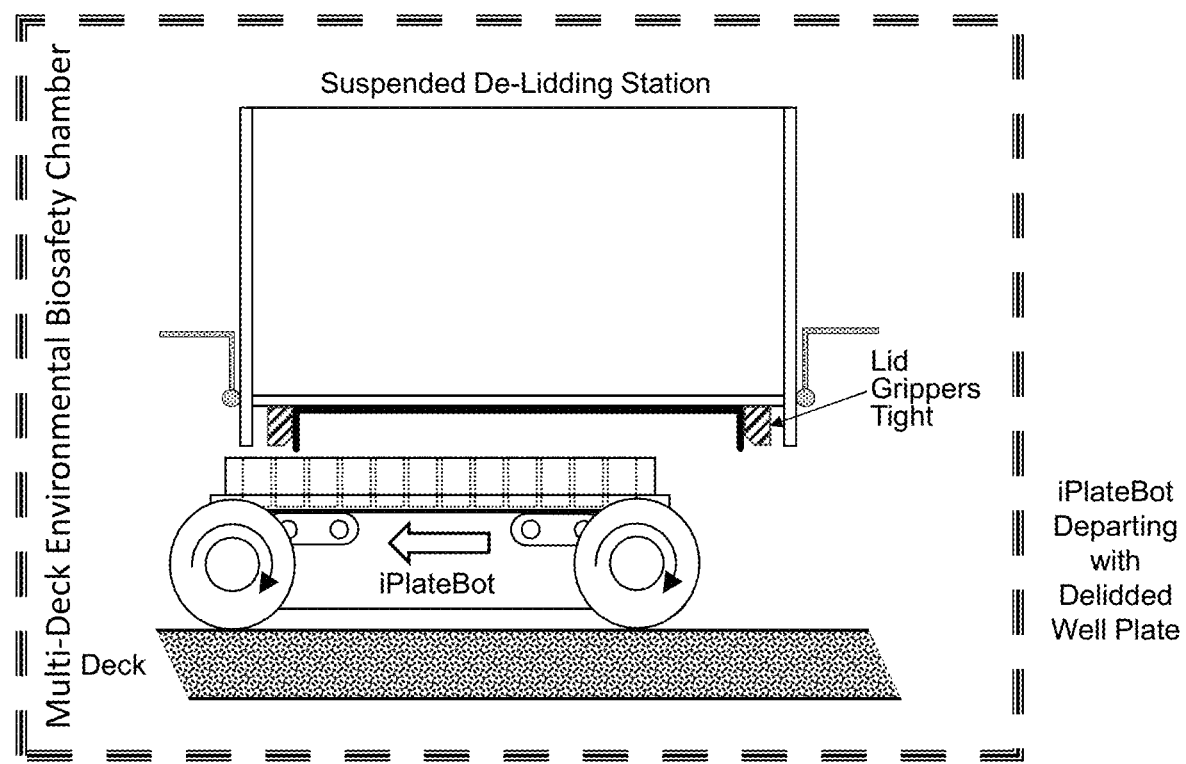
Figure 9D:
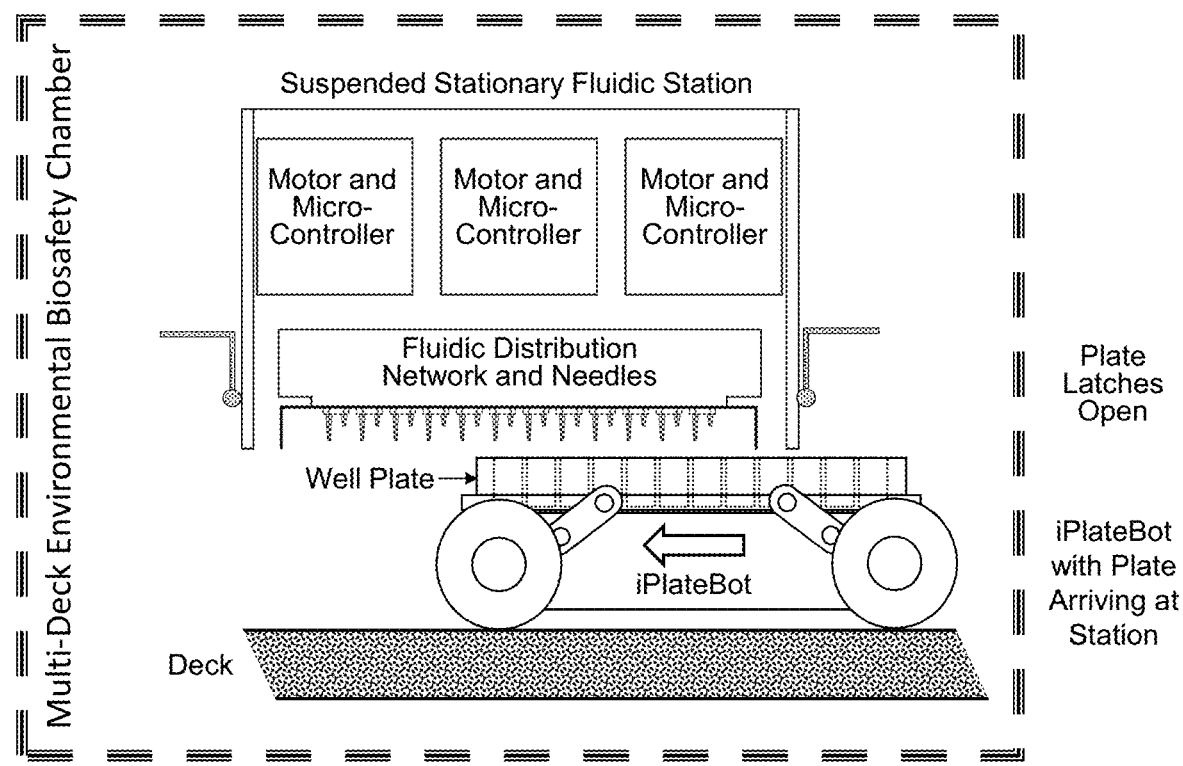
Figure 9E:
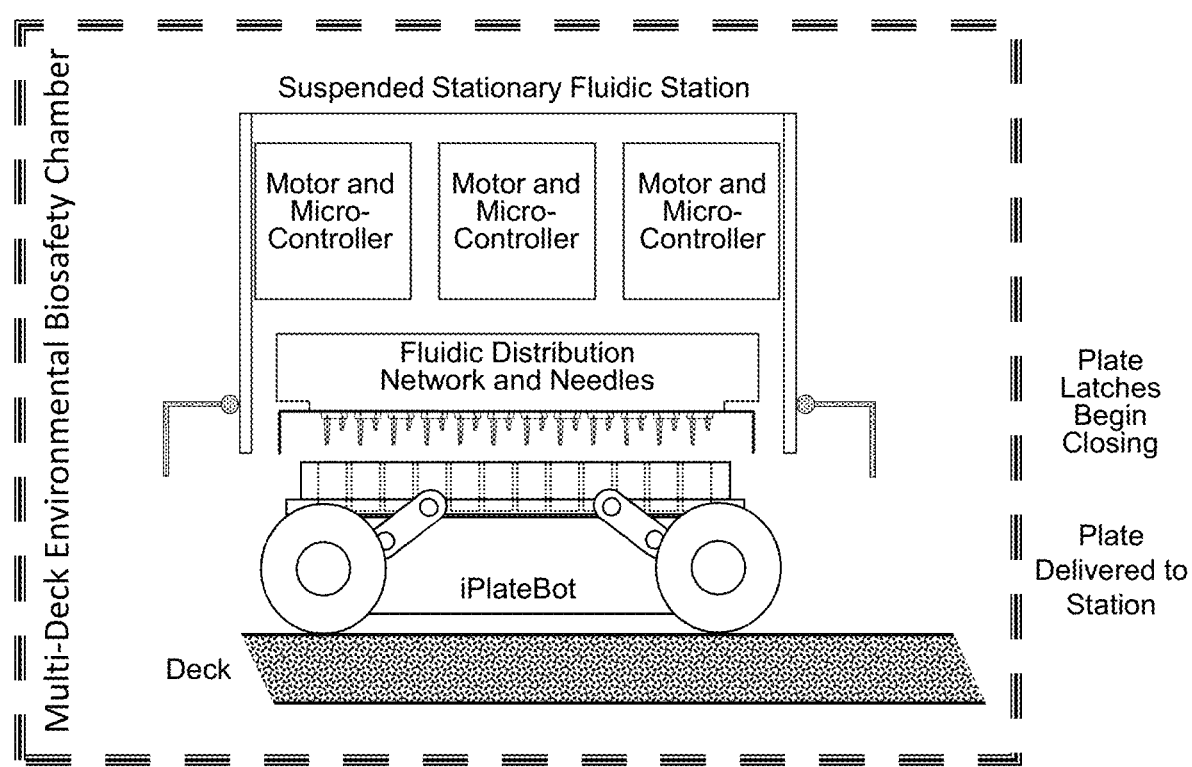
Figure 9F:
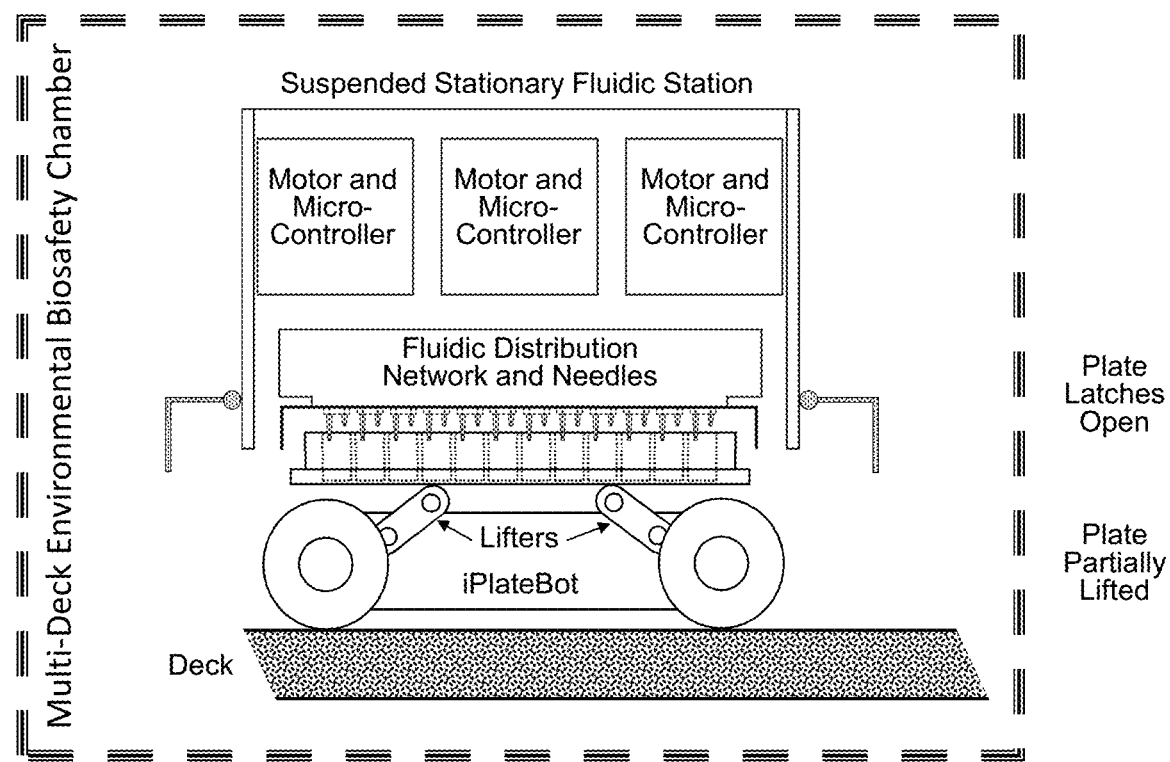
Figure 9G:
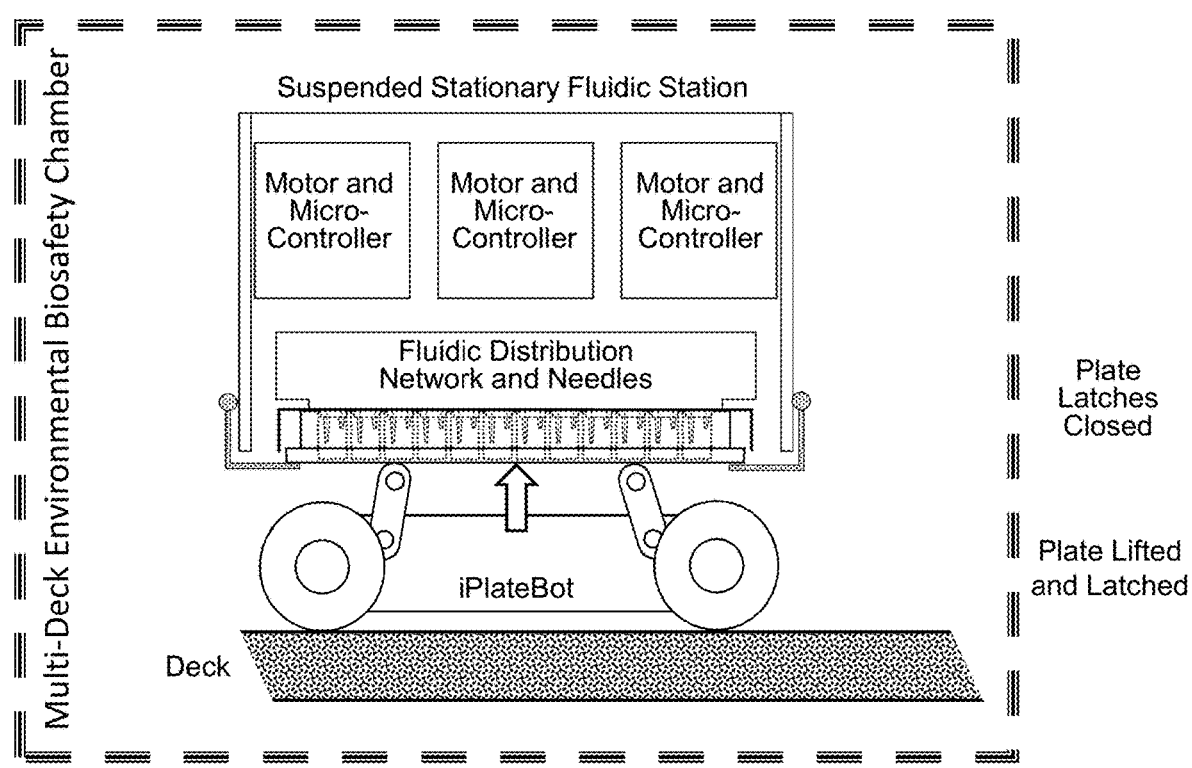
Figure 9H:
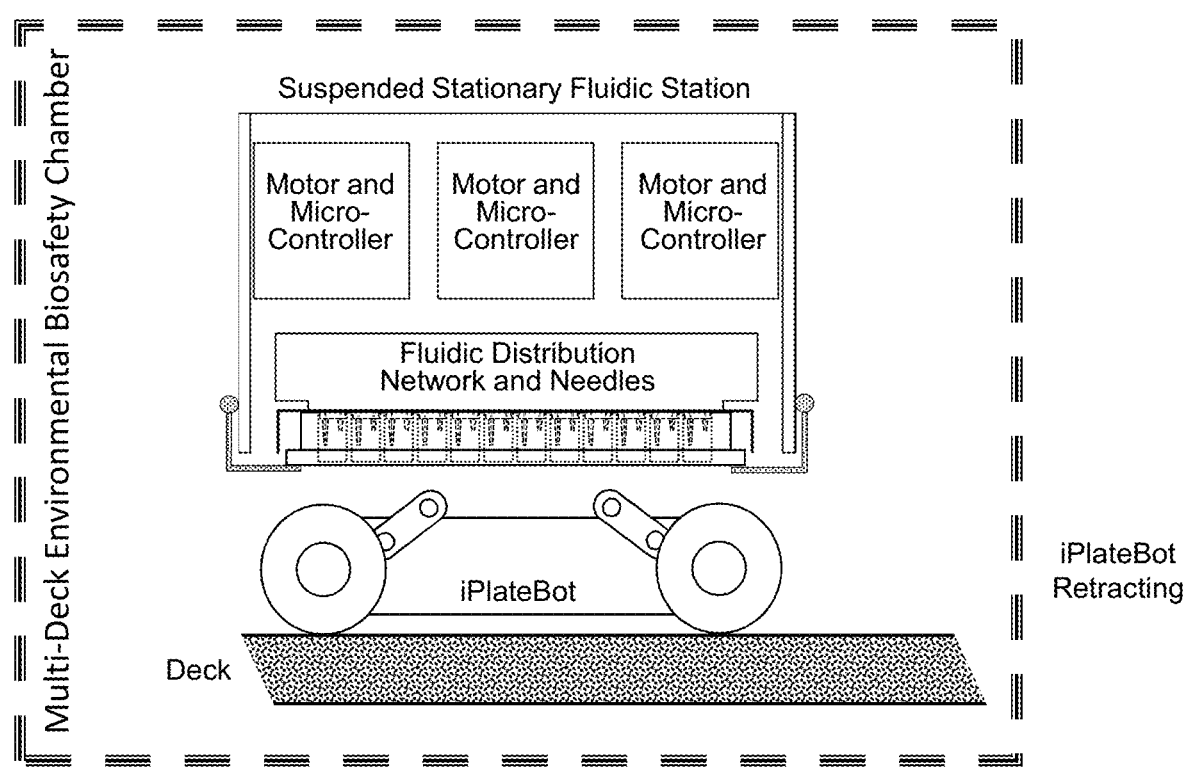
Figure 9I:
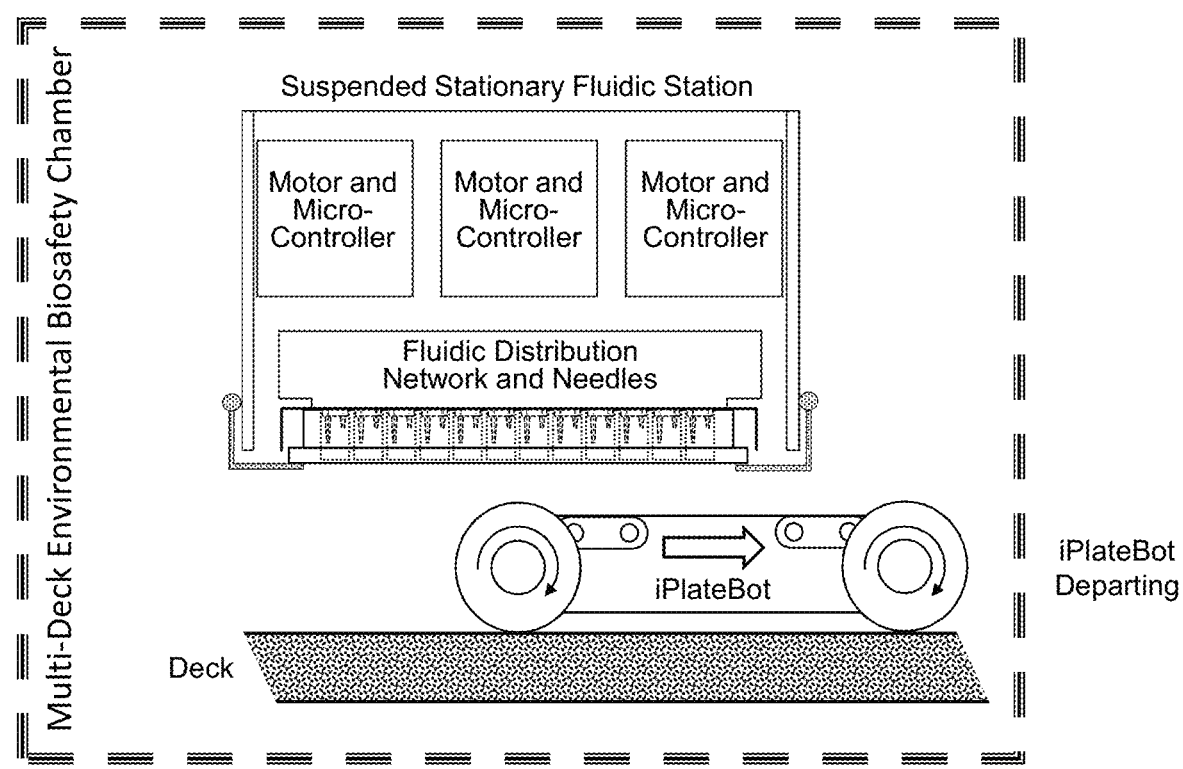

FIG. 9A shows an iPlateBot approaching a de-lidding station while carrying a well plate with a lid, where the lid grippers are loose. FIG. 9B shows the iPlateBot after lifting the well plate with lid, after which the lid grippers capture the lid. FIG. 9C shows the iPlateBot departing the station with a de-lidded well plate. The fact that these operations are being performed in CAPCAS's HEPA-filtered, sterile cell-culture enclosure minimizes the risk of contamination of the cultures in the wells for the brief time required to transport the open well plate to the adjacent fluidic interface station. FIG. 9D shows the de-lidded plate approaching the fluidic interface station, with the plate latches open. When the plate is beneath the station in FIG. 9E, the plate latches begin to close. FIG. 9F shows the plate being lifted and in FIG. 9G the plate is captured by the latches and long-term perfusion can be performed on the wells in the plate. FIGS. 9H and 9I show the lifting arms being retracted and the iPlateBot departing for another assignment. The space beneath the suspended and captured well plate is now available for the movement of other iPlateBots to other stations.

Figure 9J:
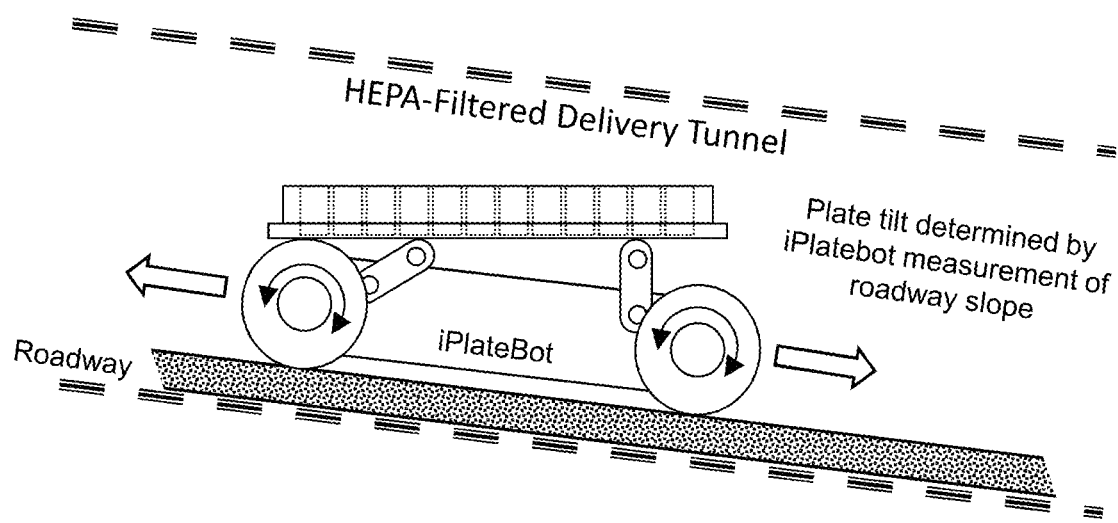
Figure 9K:
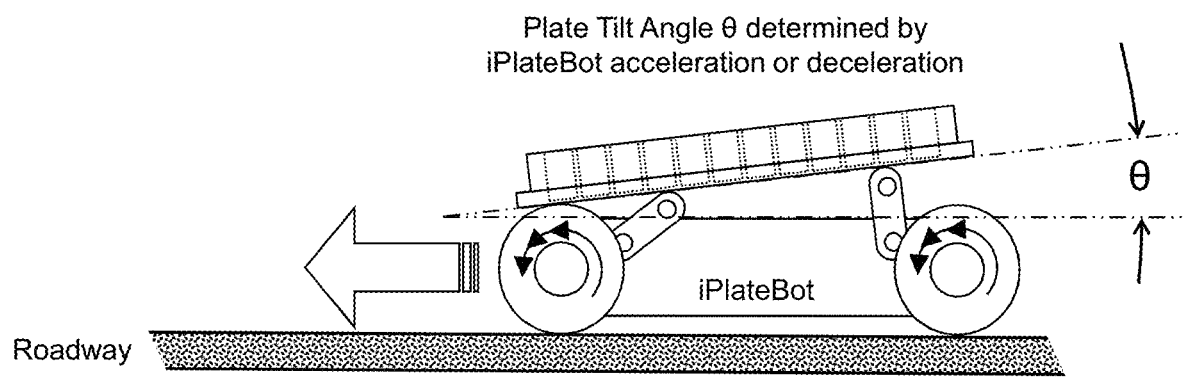

FIG. 9J shows how the lifting arms can adjust for tilt of a roadway or deck while an iPlateBot is transporting its cargo between distant stations through a sterile delivery tunnel. FIG. 9K shows how the predicted and tightly controlled acceleration of the iPlateBot can be used to control the tilt of the well plate to avoid sloshing of the contents of each well.

As another objective of the invention, the robot is employed in a robotic system for fluid handling and transport of biodevices. Specifically, the entire robotic system in one embodiment comprises a rack-type incubator having a plurality of decks, each deck having a plurality of stations, each station being configured to accommodate a perfusion module or a cell growth and plate inoculation module; and one or more robots, each robot being a holonomic robot configured to carry and load a biodevice to a desired module, wherein the rack-type incubator is configured such that two or more robots are simultaneously operable on a deck without interference. The one or more robots are operable either as a single unit or in combination as a swarm. The biodevices comprise well plates, chemostats, organ chips, transwell-plates, or other fluidic reservoirs that are contained in a multi-element biodevice array.

Figure 10A:
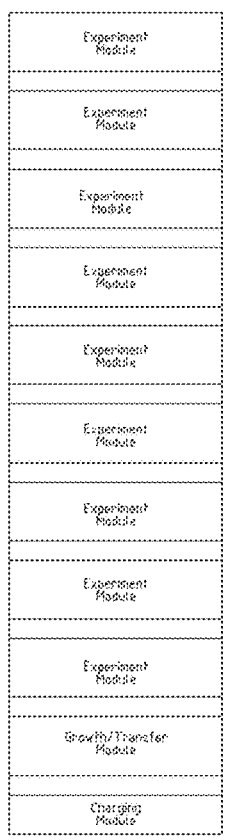
FIGS. 10A-10C show how the robot operates in a CAPCAS enclosure, according to embodiments of the invention.
Figure 10B:
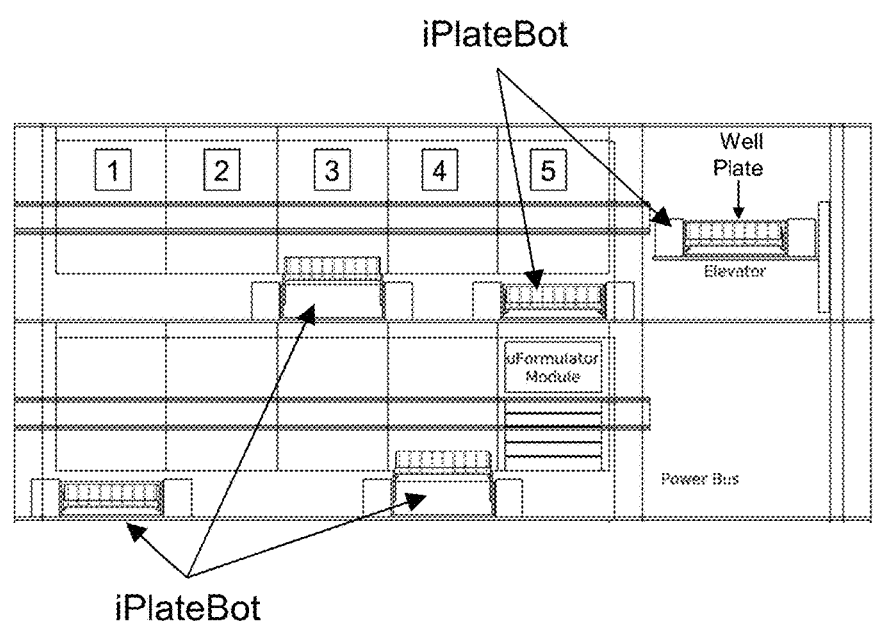

FIGS. 10A-10B show one embodiment of a robotic system rack for fluid handling and transport of biodevices, which showing how modules can be positioned and serviced in the system rack. In FIG. 10A, the system is installed in a 42 U telecom/server rack, where one "U" or rack unit is a measurement of the height of a piece of computer or network gear that is designed to fit into a standard 19" or 23" electronics rack. In the rack, this embodiment has nine experiment modules that are 4 U tall and have 12 plates each. One module in the rack will be dedicated to cell growth and plate inoculation, and another will be dedicated to charging the iPlateBot robots. In an alternative embodiment, a charge-in-place scheme will be implemented on the plate receiver modules. The rack is insulated and appropriately sealed so that it also acts as a sterile cell culture incubator.

FIG. 10B shows one possible configuration for two of the 4 U segments of a telecom/server rack incubator: Stations 1-4 are plate receiver modules for plate perfusion, while Station 5 has a fluidic MicroFormulator to provide mixed media to all modules on the level plus storage space for lids. Each level can be connected to a continuous circulation fluid bus and a power bus. In this exemplary embodiment, an elevator is adapted for moving a robot between decks.

Figure 10C:
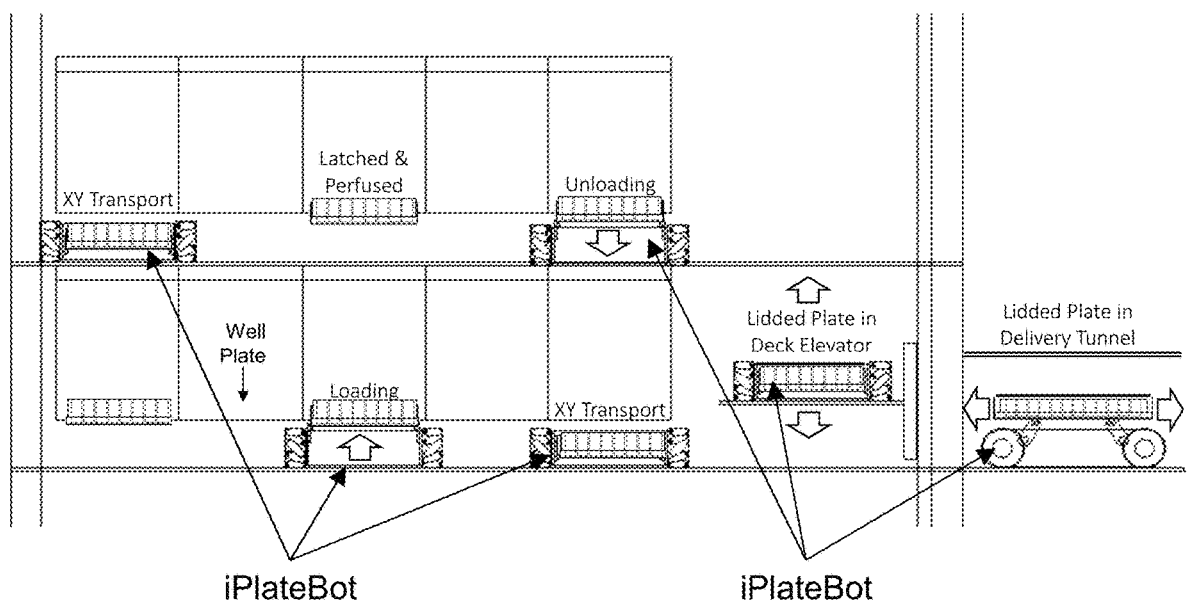

FIG. 10C shows iPlateBots in an automated incubator. The iPlateBot delivers a plate to an assigned fluidic station in the incubator. The plates are raised and latched into the fluidic handling station. The iPlateBot departs for another assignment with the elevator, and if the plate it is carrying is needed outside the incubator, the iPlateBot can depart through a delivery tunnel. The fact that a large number of independent iPlateBots can operate within a single enclosure and move both vertically and horizontally in an asynchronous, swarm-based manner enables a level of parallel plate-processing that cannot be achieved in a HTS robotic system which might have at most several different robot arms, each of which can serve only a fraction of the footprint of the HTS system. Plates that are in use either for compound or cell delivery, as active chemostats, or plates that collect cells and media for analysis are suspended from above, leaving the space beneath each plate open for an iPlateBot to move in the X or Y directions on that deck. If a 12-position deck has, for example, nine fluid-handling stations, a plate-filling station, and two lid storage areas, multiple iPlateBots can move between any of these stations and also pick up and deliver plates at stations on other decks in the enclosure or even to other enclosures or work stations connected by tunnels or transiently opened drawers.

Figure 11:
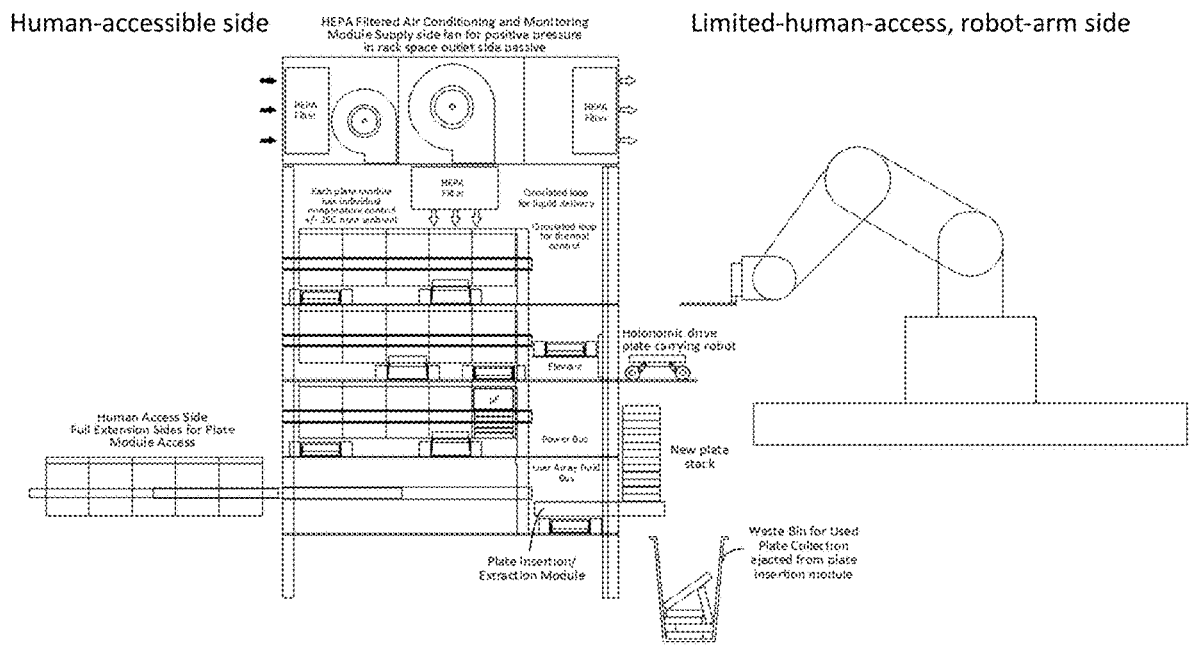
FIG. 11 shows how the robot operates in a CAPCAS enclosure and interface with both human operators and a high-throughput screening robot arm, according to embodiments of the invention.

FIG. 11 shows the iPlateBots operating in a rack that is fully equipped to serve as an environmental chamber, with complete control over temperature, gas composition, and humidity, with HEPA filtering to maintain sterility. The human access side can be opposite to that serviced by the robot arm to protect the human operators.

Figure 12A:
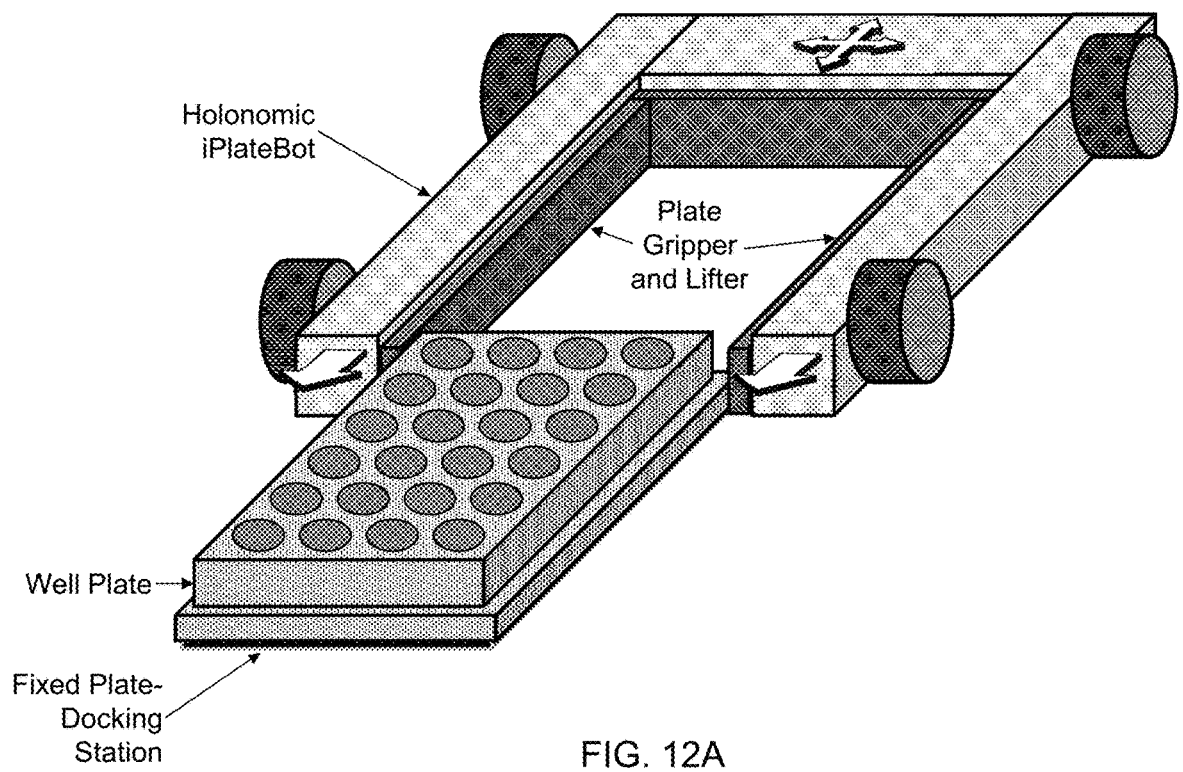
FIGS. 12A-12D show how the robot approaches a well plate, lifts it from its stationary dock, and transports it to another location, according to embodiments of the invention.
Figure 12B:
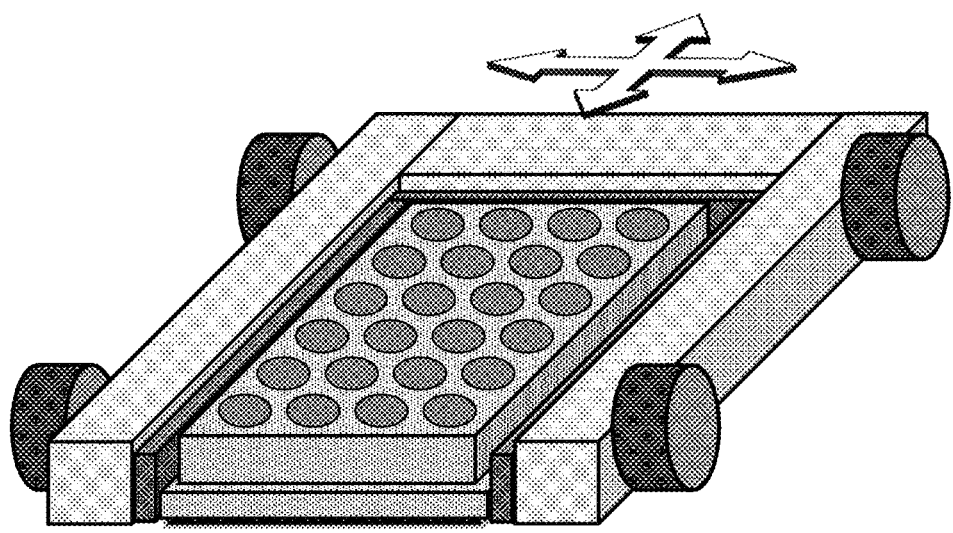
Figure 12C:
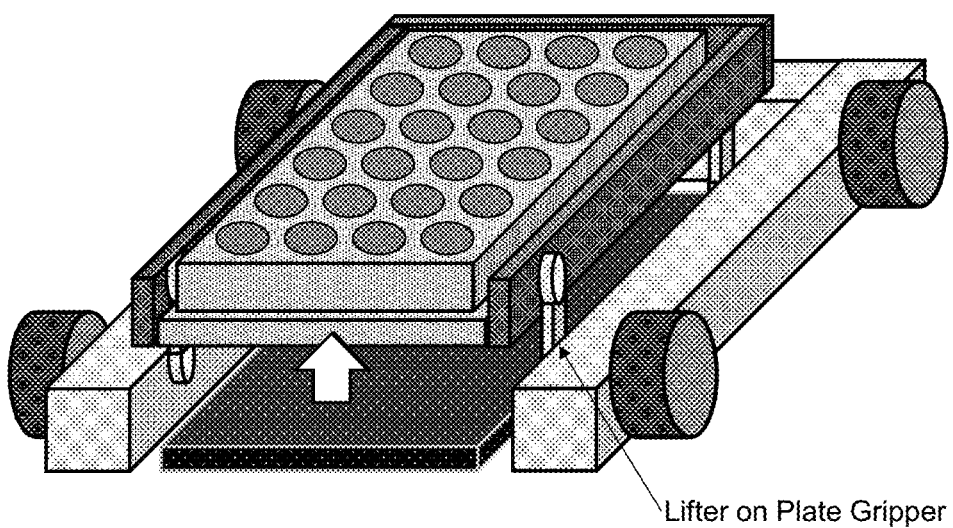
Figure 12D:
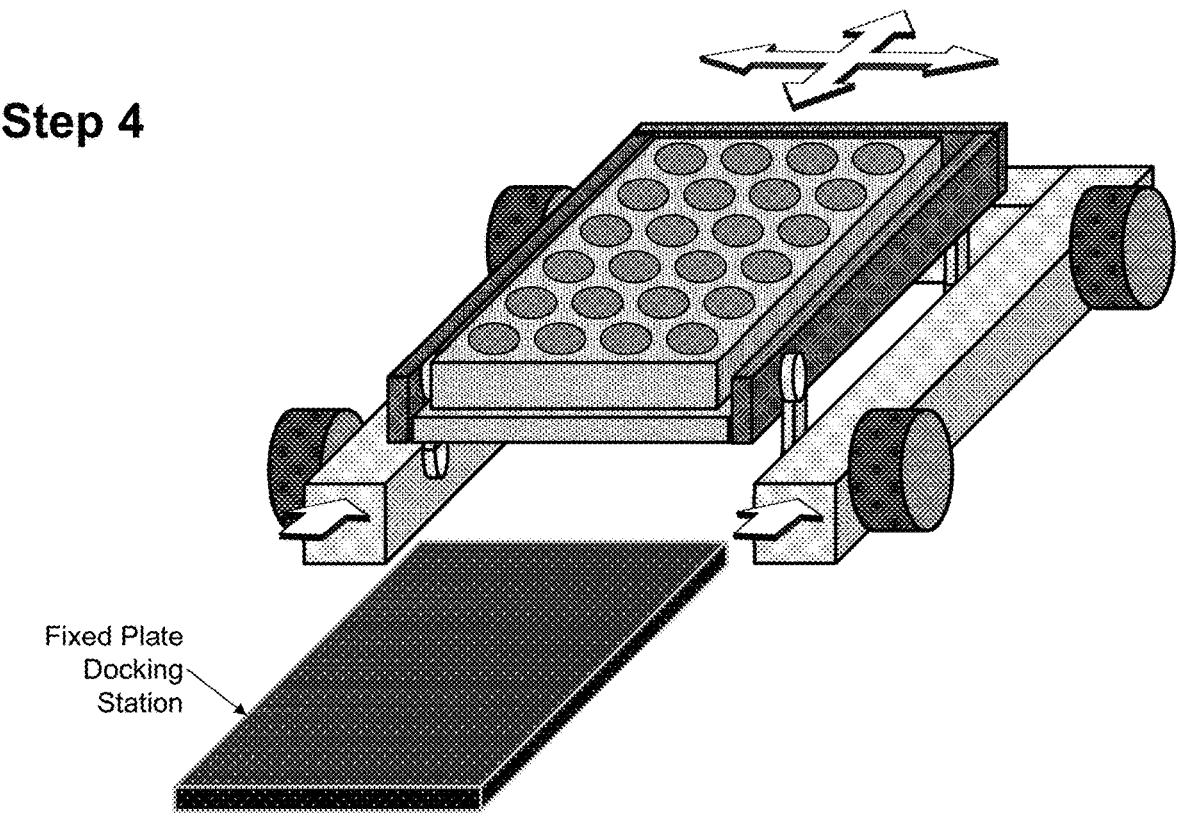

When interfacing the iPlateBot with an external robot arm, the arm can deposit the well plate at a fixed plate-docking station. FIGS. 12A-12D show the sequence of events when an iPlateBot is instructed to travel to that station, pick up the plate, and transport it to another location. As shown in FIG. 12A, at Step 1, the iPlateBot moves toward the well plate at the fixed plate-docking station so as to accommodate the well plate in the central space (e.g., 160 in FIG. 2), then grips both the well plate and the fixed plate-docking station and moves to the desired location at Step 2, as shown in FIG. 12B. At Step 3, when arriving at a place and arrive with the correct orientation, which may be proximate to the desired location, the gripper and lifter of the robot lifts the well plate, as shown in FIG. 3. Next, the robot leaves the fixed plate-docking station, and moves to load the well plate to the desired location at Step 4, as shown in FIG. 12D.

Figure 13A:
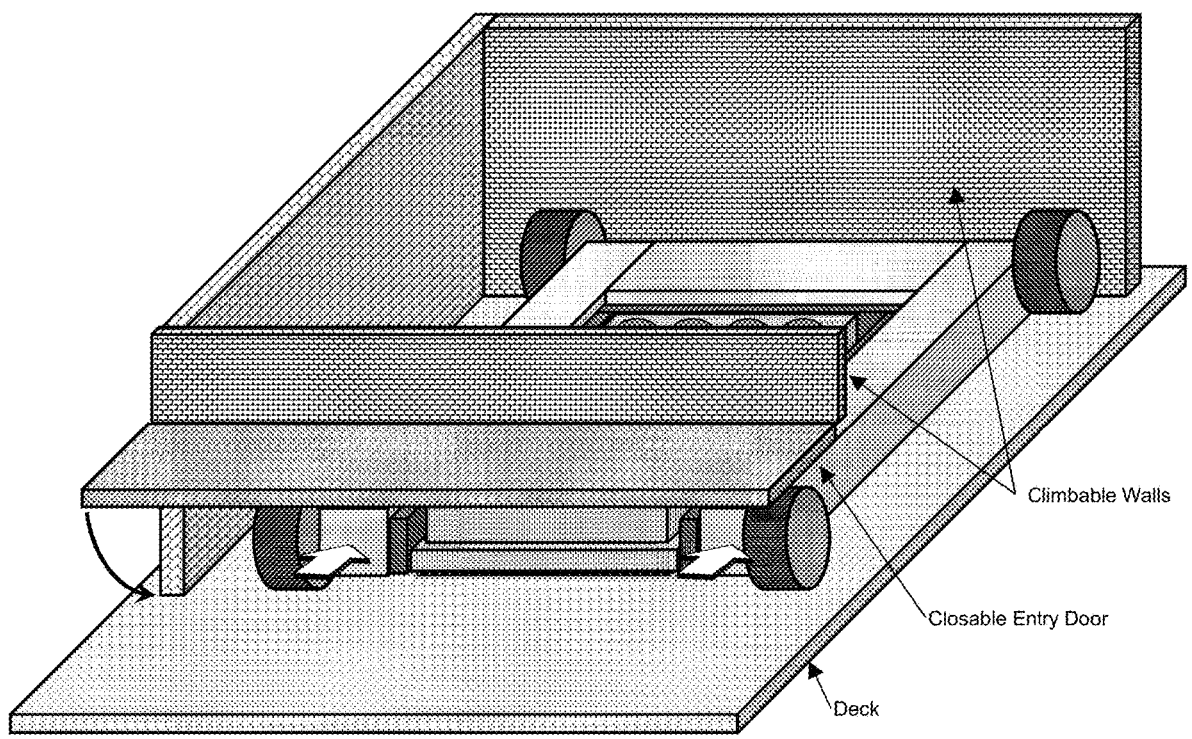
FIGS. 13A-13B show how the robot climbs a vertical shaft instead of requiring an elevator, according to embodiments of the invention.
Figure 13B:
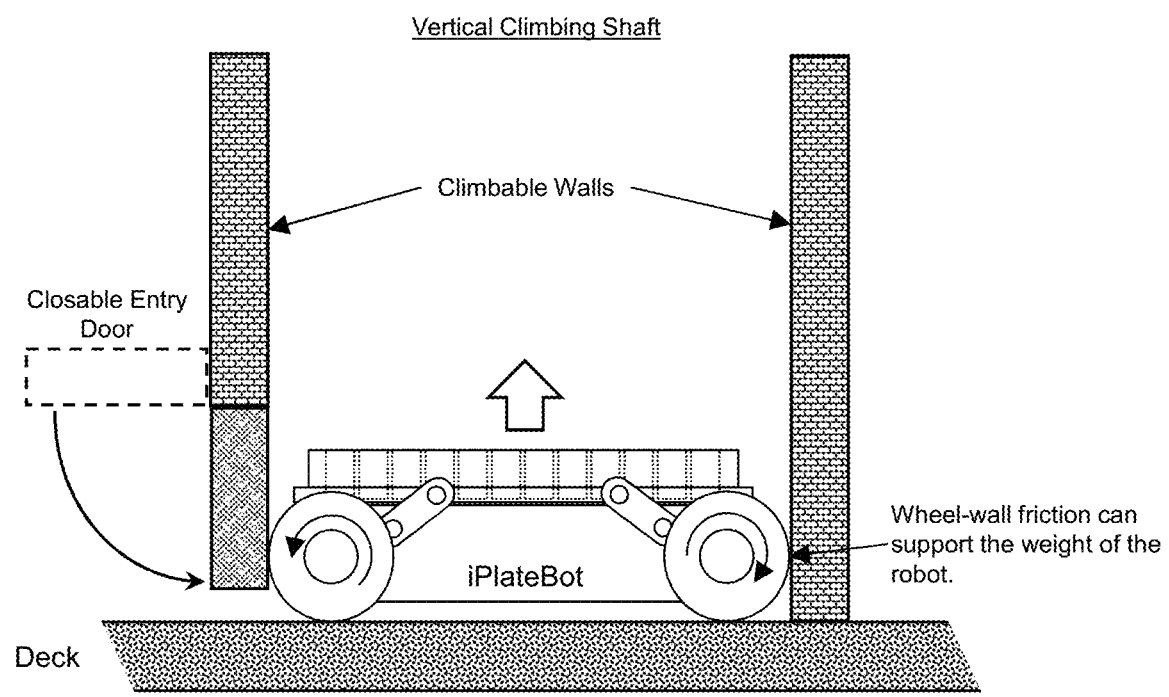

FIGS. 10B and 10C show how an elevator could transport an iPlateBot and its cargo between decks. FIGS. 13A and 13B present an alternative embodiment, in which the iPlateBot wheels extend beyond the ends of the side plates such that they can grip vertical walls. As shown in FIG. 13A, the iPlateBot has driven into a vertical shaft and a closeable entry door is about be lowered and in doing so compress slightly the four wheels against the two vertical surfaces. The ability of the walls to support a climbing iPlateBot can be enhanced by texturing or even corrugating the wall surface for positive engagement of the four wheels. Tilt sensors within the robot would allow the automatic controls to adjust one or more motor speeds to ensure that the cargo remains level as it is being transported within the shaft. FIG. 13B shows an alternative view of the vertical climbing shaft. The horizontal distance between the two walls is designed to ensure that the elastomeric wheels are sufficiently compressed that the wheel-wall friction can support the weight of the robot. The door-closing mechanism hence has to have the strength to compress the wheels slightly when closing the door. Not shown is a mechanism at the top of the shaft where, upon arrival at the destination height, a folding or sliding support structure or shelf is engaged to prevent the robot from dropping when the exit door is opened. The process would function in reverse to lower the robot back to the original deck.

Figure 14A:
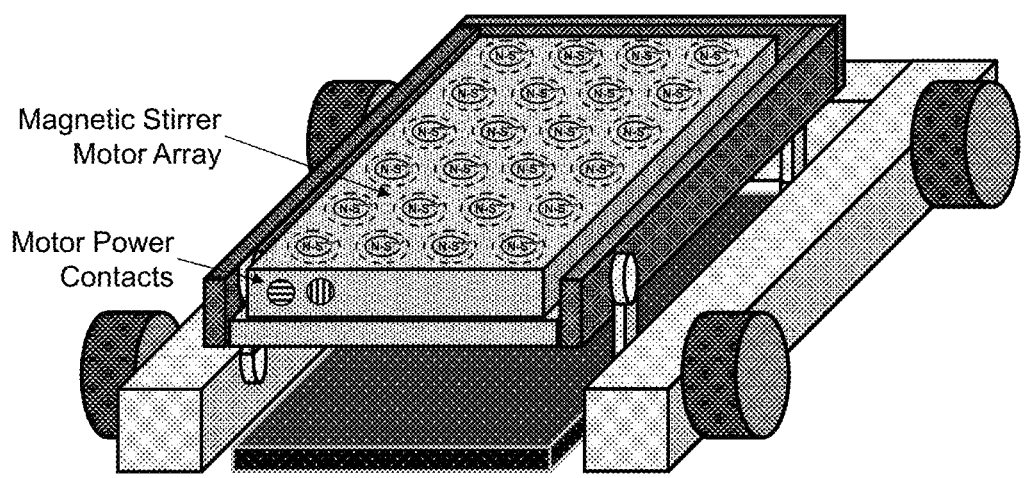
FIGS. 14A-14C show how the robot transports and delivers a multi-well magnetic stirrer for long-term unassisted operation beneath a well plate in a CAPCAS enclosure, according to embodiments of the invention.
Figures 14B, 14C:
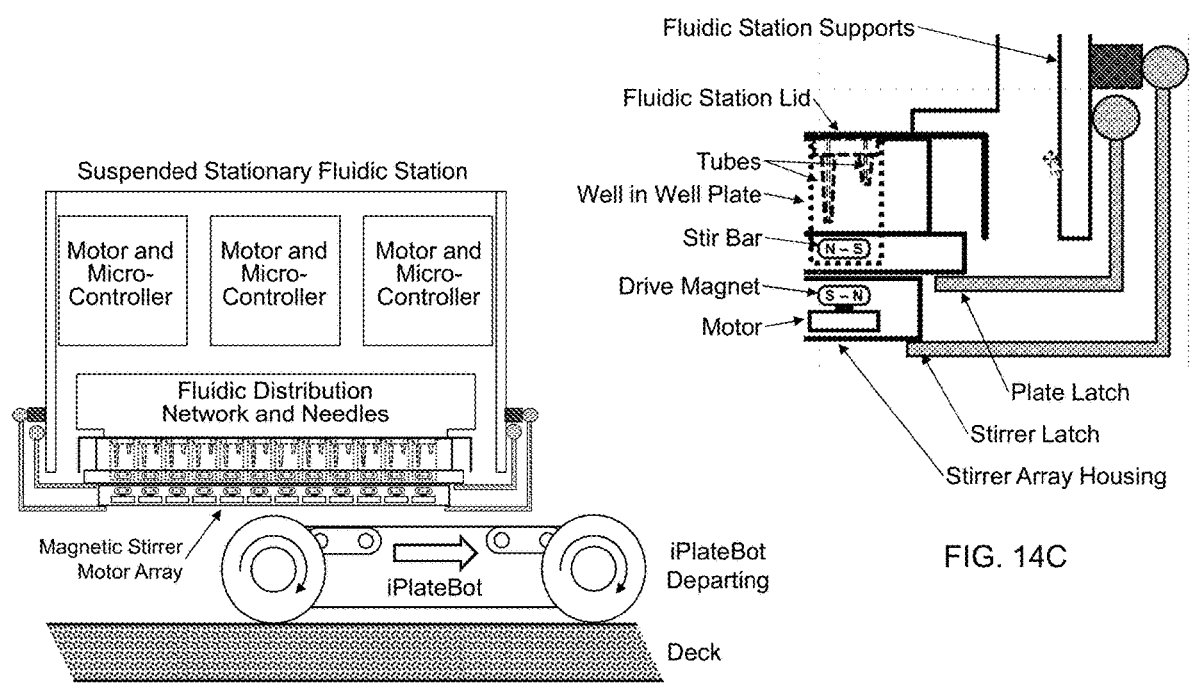

FIGS. 14A-14C show how the iPlateBot could deliver a magnetic stirrer array that contains low-profile motors and rotating permanent magnets underneath a well plate into which each well has been inserted a small magnetic stir bar.

Figure 15:
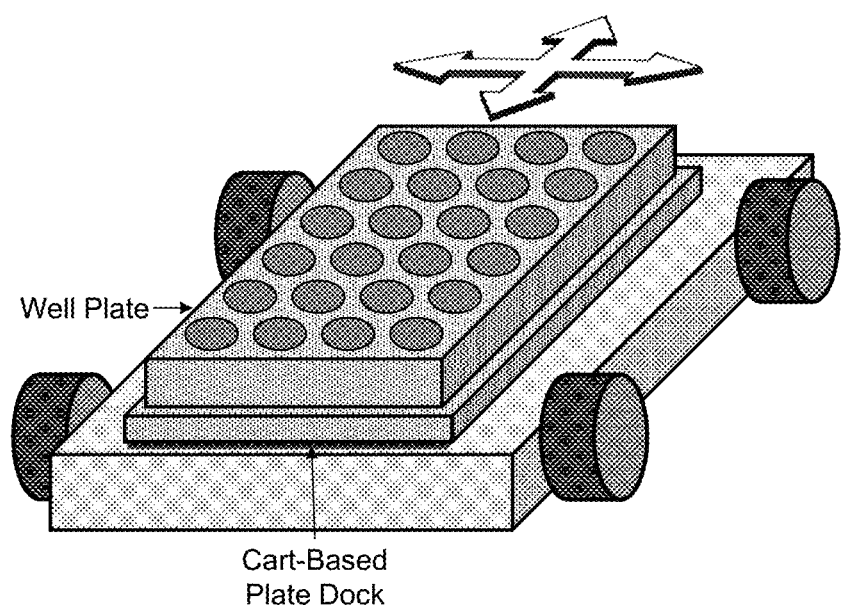
FIG. 15 shows the robot with a flat top and a cart-based plate dock, according to embodiments of the invention.
Figure 16A:
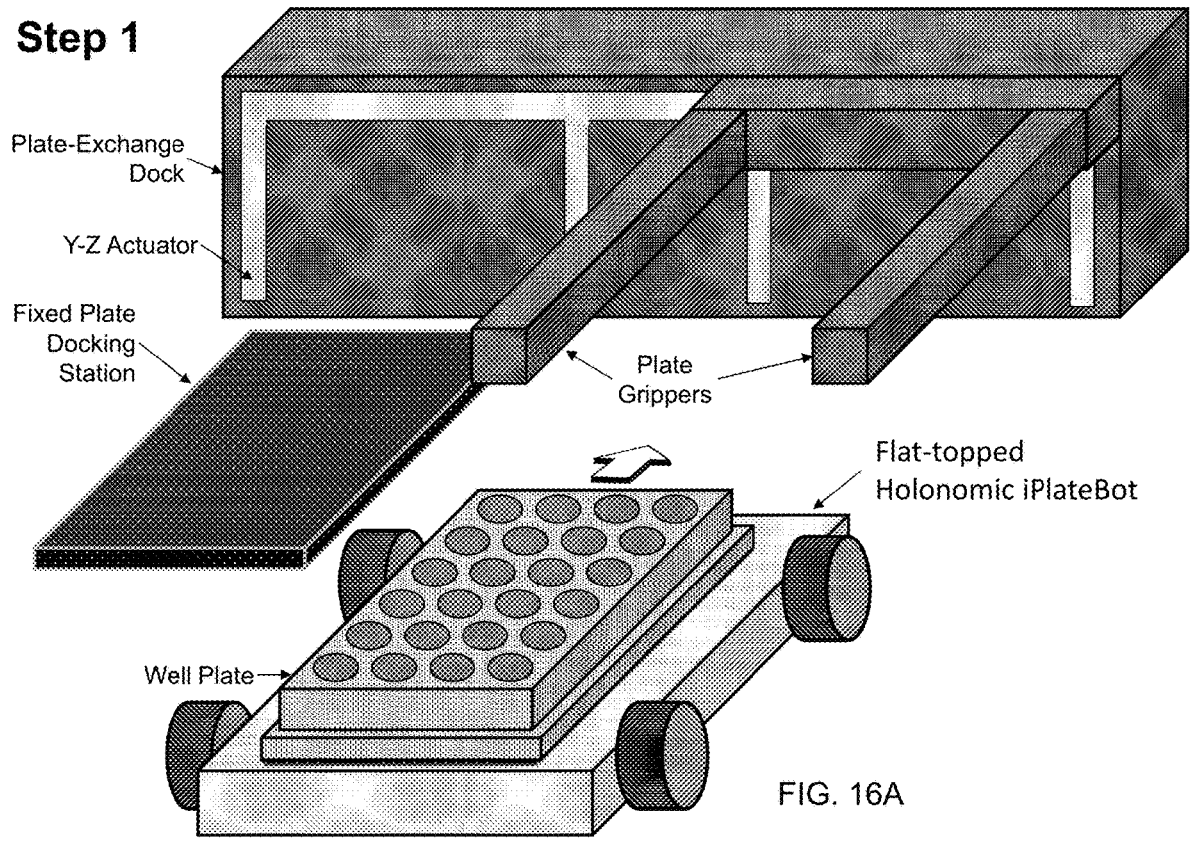
FIGS. 16A-16K show a plate-exchange dock that can transfer a plate to or from a fixed plate docking station to the subject invention, according to embodiments of the invention.
Figure 16B:
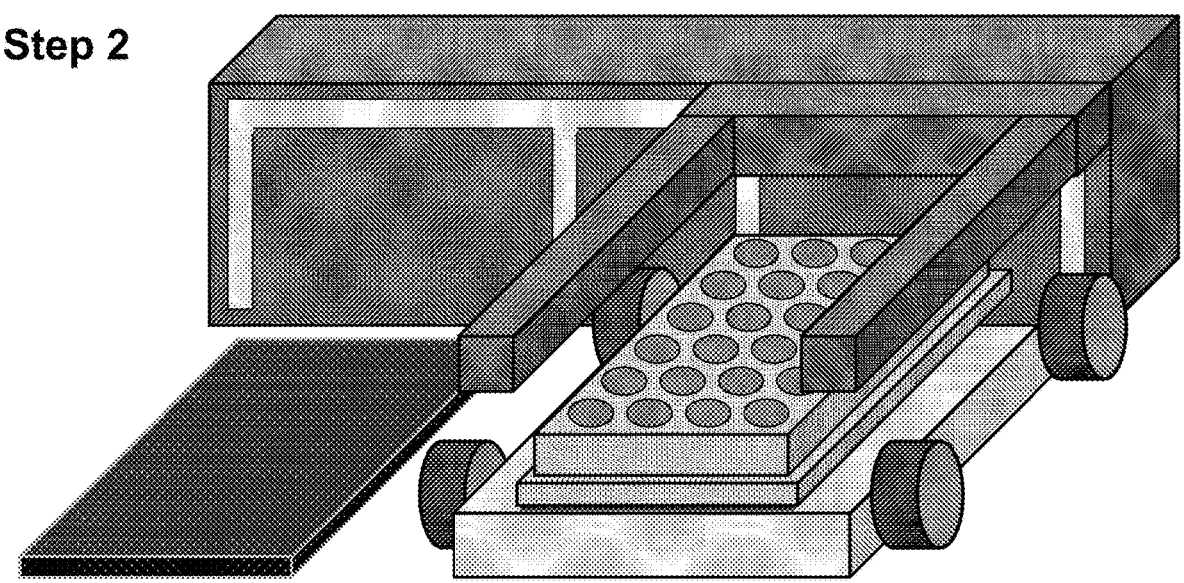
Figure 16C:
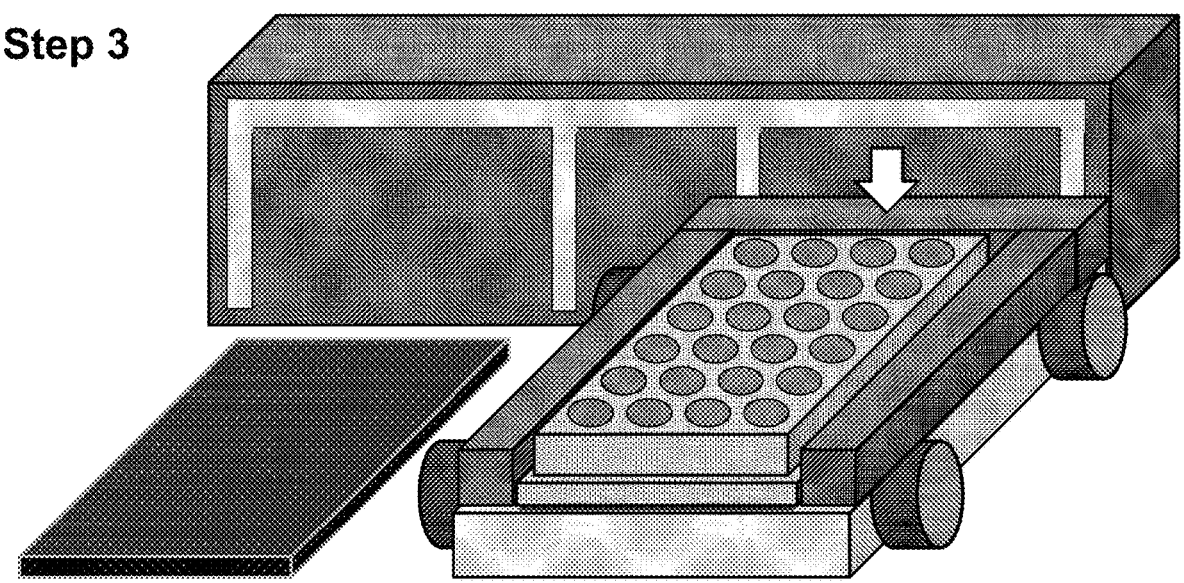
Figure 16D:
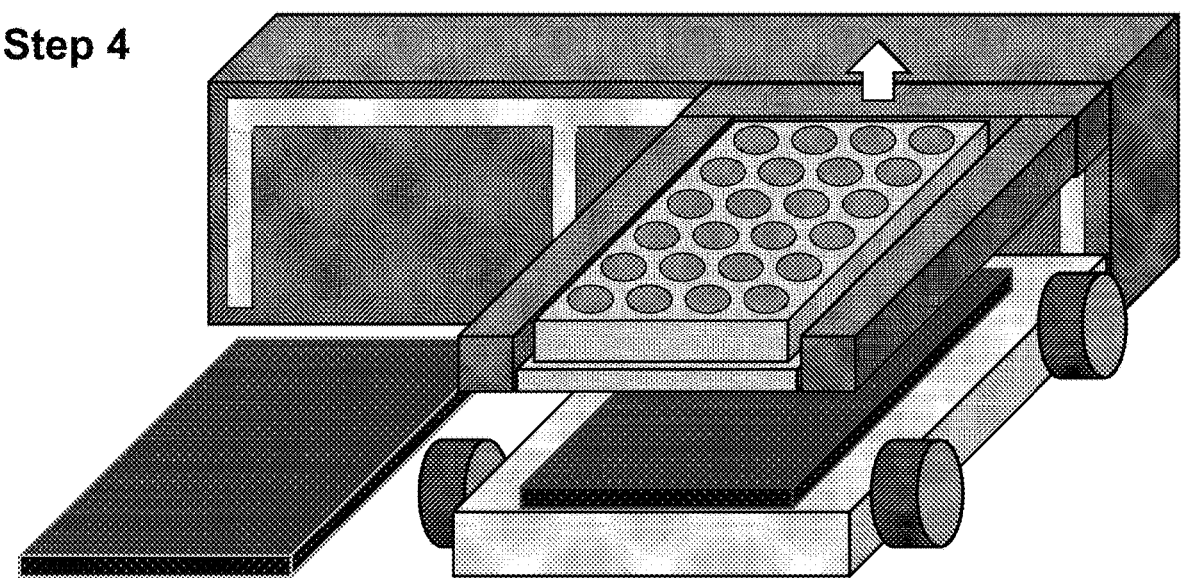
Figure 16E:
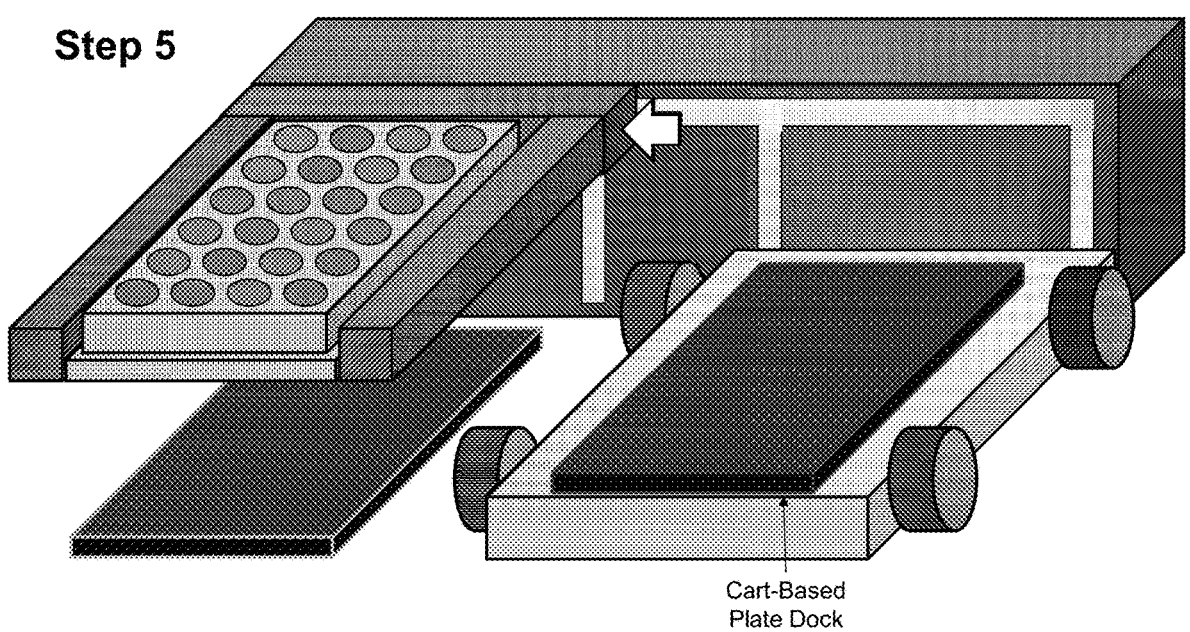
Figure 16F:
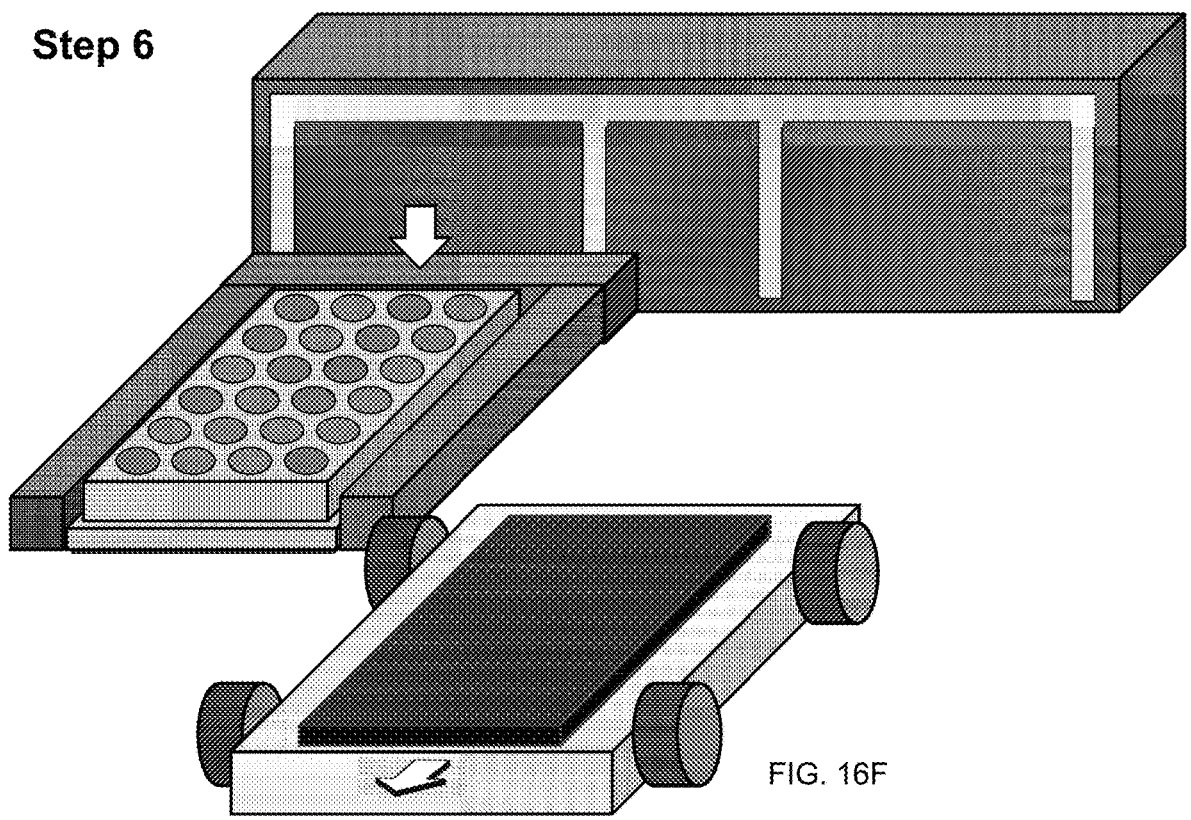
Figure 16G:
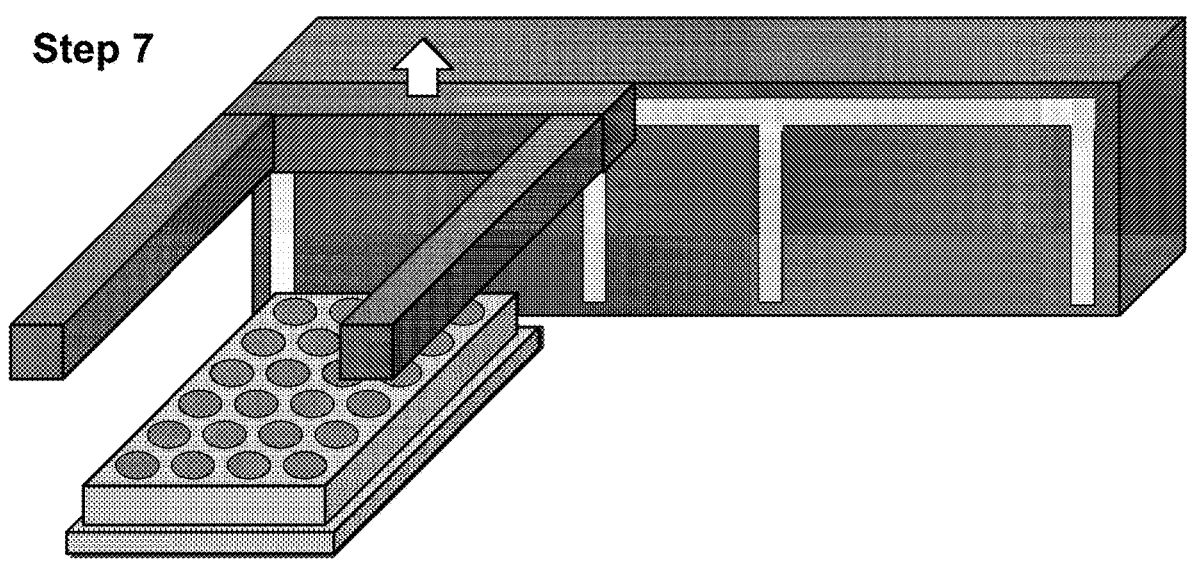
Figure 16H:
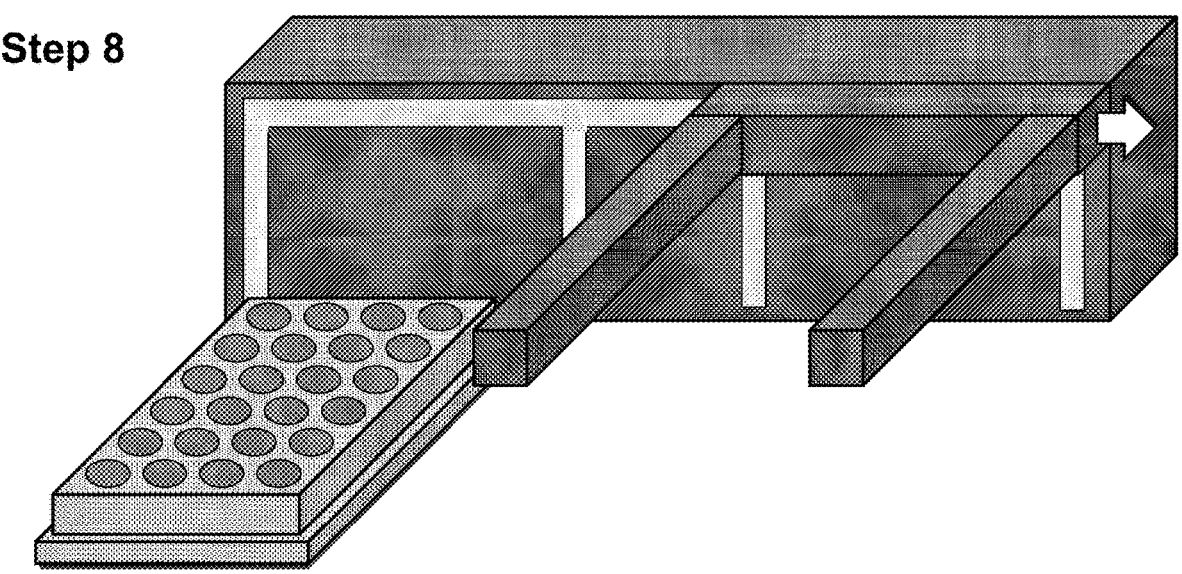
Figure 16I:
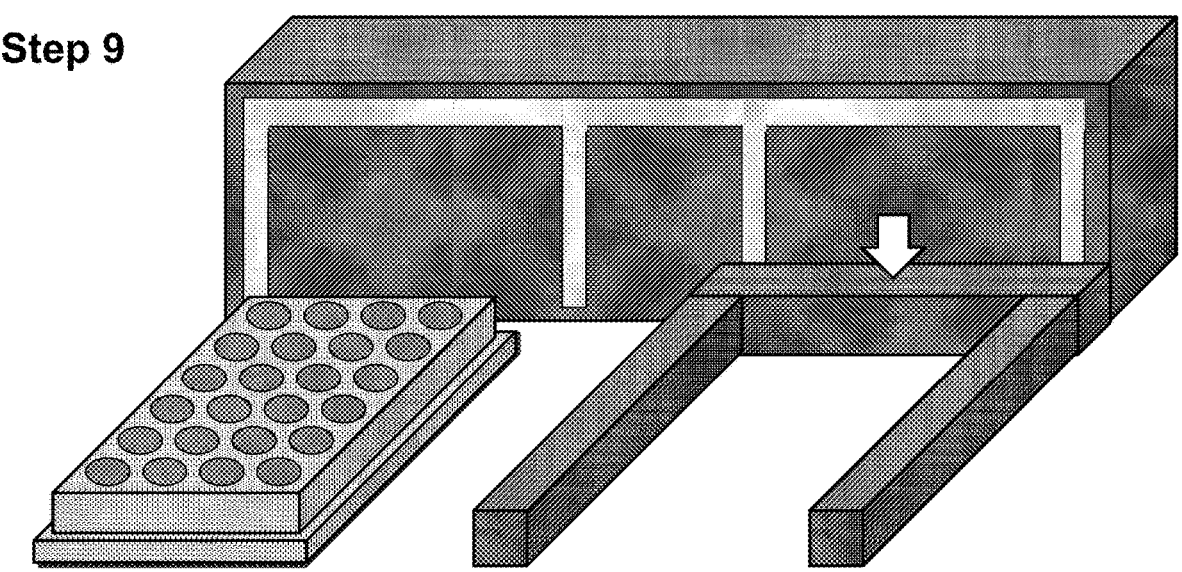
Figure 16J:
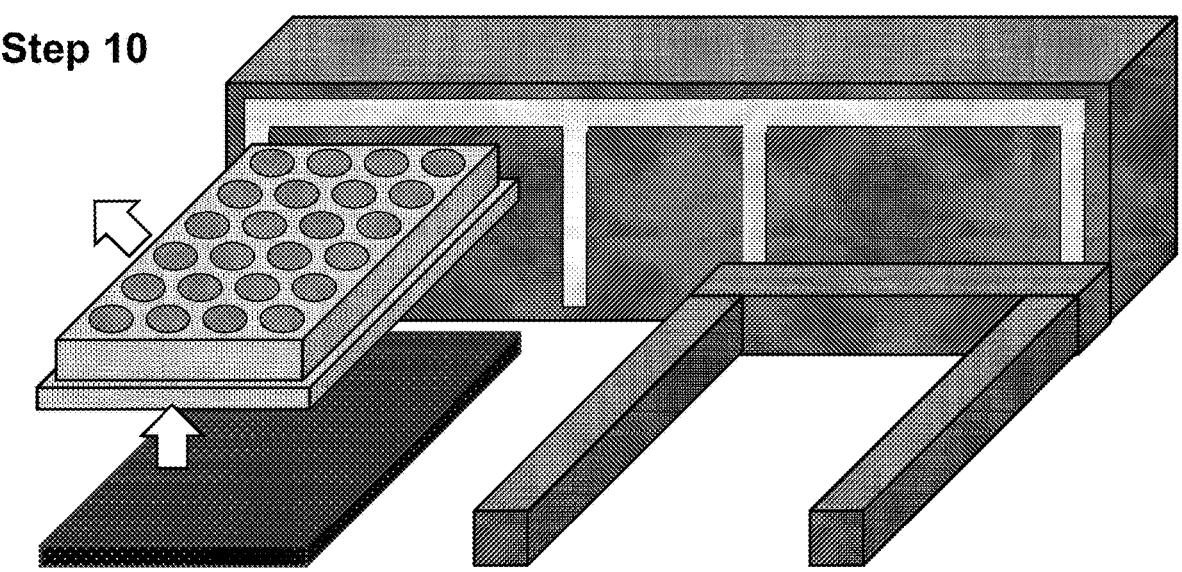
Figure 16K:
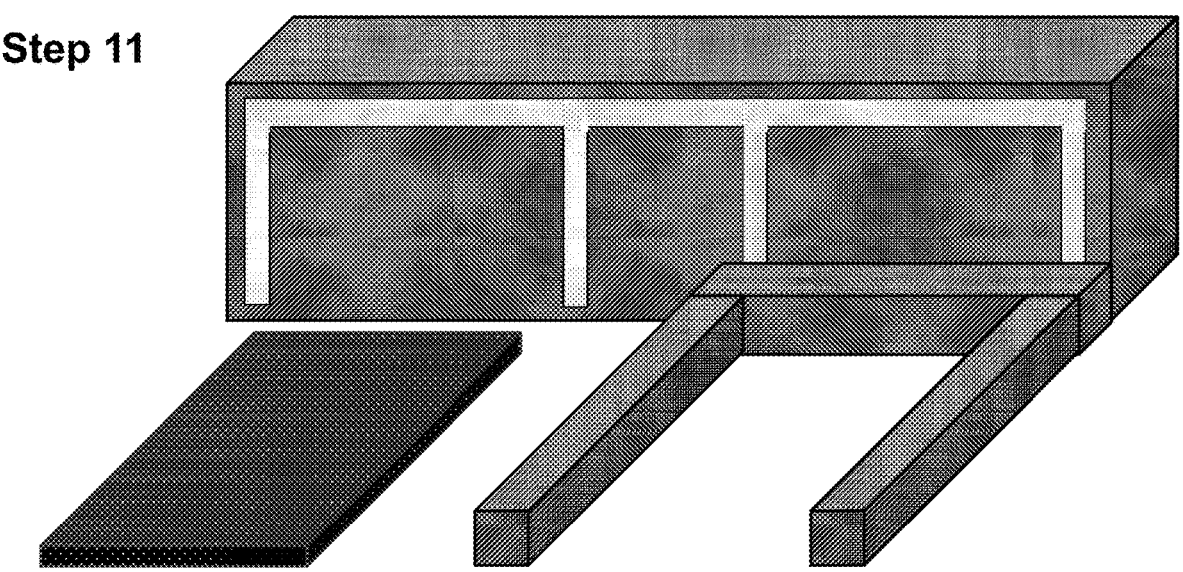

FIG. 15 shows a flat-topped robot whose upper surface contains a cart-based plate dock. This holonomic robot can move in any direction in the XY plane, albeit without the low height required to operate between decks in the CAPCAS enclosure. Such a robot might be ideal for long-distance transport between work stations.

FIGS. 16A-16K show a plate-exchange dock that can transfer a plate to or from a fixed plate docking station to the subject invention, according to embodiments of the invention. In this exemplary embodiment, the plate-exchange dock includes plate grippers and a Y-Z actuator configured to move the plate grippers in Y and Z directions, such that the plate grippers can grip a well plate from one place, e.g., one iPlateBot, move to another place and load the well plate thereon, and vice versa. This system could be utilized by a variety of robots. The fixed plate docking station in FIG. 16A would be a location where an HTS arm might deposit a well plate to be picked up by a flat-topped iPlateBot that could not straddle the docking station. The sequence of events shown in FIGS. 16A-16J culminates with the plate being removed from the dock by a human or robot arm. At the end of the operation (FIG. 16K), the docking station is vacant for a future operation.

Figure 17:
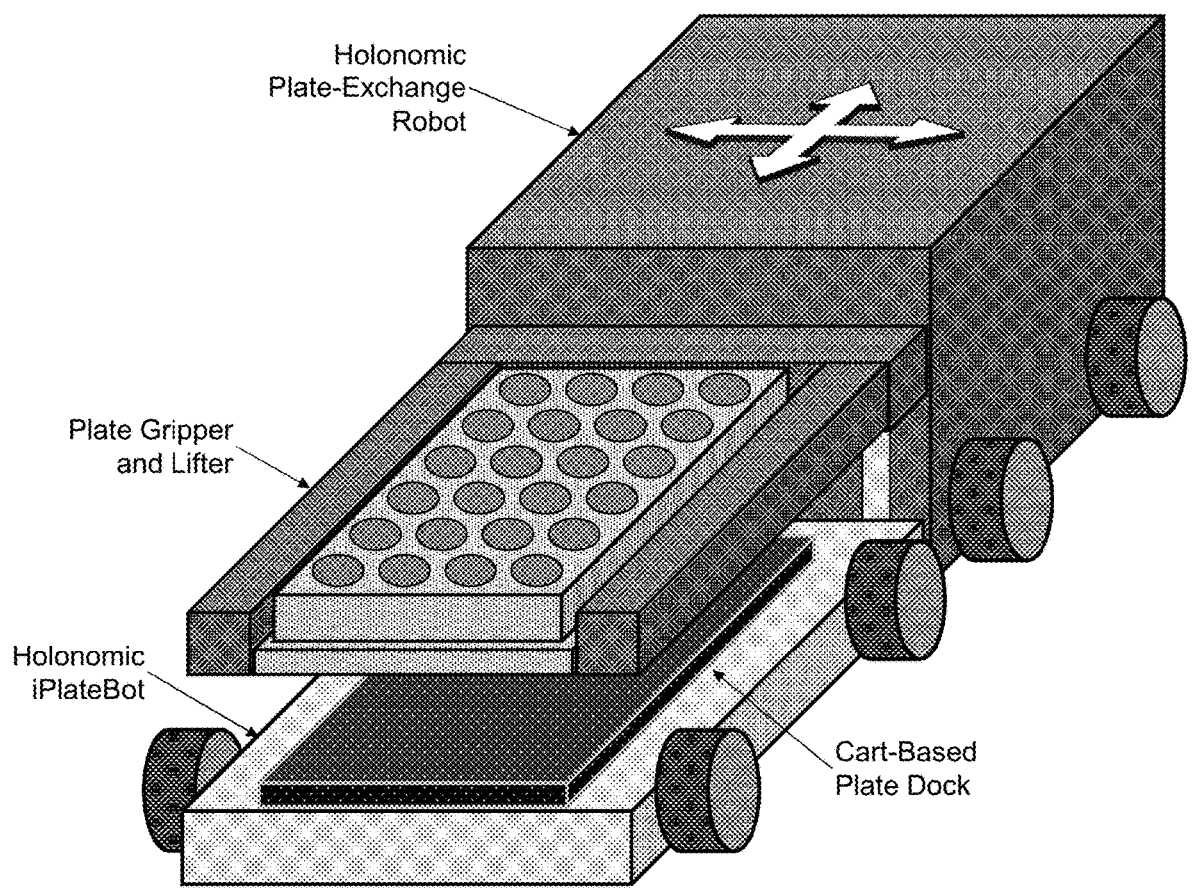
FIG. 17 shows an embodiment of the robot operating as a mobile plate exchange system, according to embodiments of the invention.

FIG. 17 shows holonomic plate-exchange robot whose plate gripper and lifter extends beyond the wheeled portion of the exchange robot so that it can facilitate transfers between plates, and could also recover a plate from a disabled robot that was unable to complete its delivery.

Figure 18:
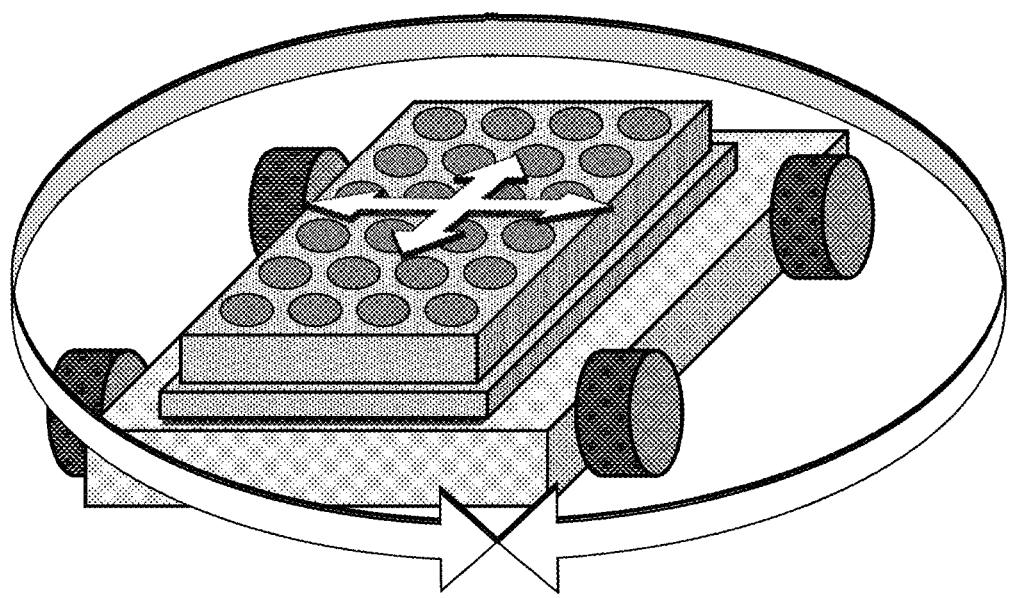
FIG. 18 shows how lateral and rotational motions of the robot can be used to stir and hence mix the contents of each well without splashing or well-well contamination, according to embodiments of the invention.

FIG. 18 shows how lateral and rotational motions of the iPlateBot can be used to stir and hence mix the contents of each well without splashing or well-well contamination, according to embodiments of the invention. In this embodiment, the iPlateBot is configured to have timed motor rotations and translations to stir the well plate, and could even have controlled tilting.

Figure 19A:
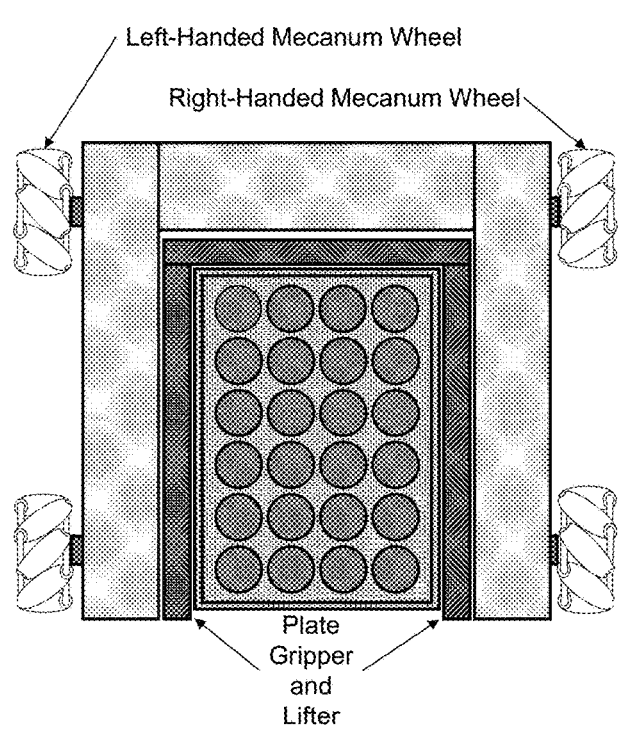
FIGS. 19A-19B show how the robot can be implemented with either four Mecanum wheels or three Omni wheels, according to embodiments of the invention.
Figure 19B:
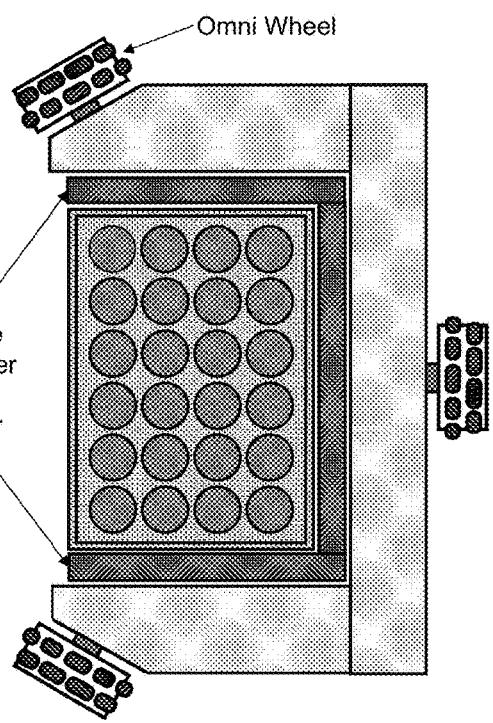

FIGS. 19A-19B show how the concepts presented in describing this invention can be implemented with either four Mecanum wheels or three Omni wheels. Any embodiments of a robot with Mecanum wheels work with Omni wheels.

FIGS. 20A-20D show how boxes that could be transported by the robot could allow the CAPCAS to perfuse one or more gravity-perfused single-chamber organ chips whose input and collection reservoirs are pipette-tips (FIG. 20A) or larger integrated reservoirs (FIG. 20B). The same concept can be used to perfuse a two-chamber barrier bioreactor (FIG. 20C) or both chambers of one well of a transwell plate. The pump and valve above each of these boxes is meant to serve as a schematic representation of a multi-channel perfusion/recirculation system. An array of such systems could be suspended above CAPCAS decks, and the iPlateBot could transport these boxes between various stations. The purpose of the boxes is to ensure sterility and humidification of the open reservoirs used to perfuse each biodevice. When the box is being transported, it is covered with a lid, just as is a well plate being transferred. When the box is delivered to the CAPCAS fluidic interface station as shown in FIGS. 20A-20D, the box can be de-lidded and lifted into position beneath a suspended fluidic interface station using the same sequence of events as shown for a well plate in FIGS. 9A-9K, with the possibility that more vertical distance will be required between the deck and the de-lidding or fluid interface stations to accommodate the height of the box being greater than a well plate. When the box is in place in the fluidic interface station, the lid built into that station will ensure sterility of the contents of the box, including the sterile reservoirs therein.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

What is claimed is:

1. A robot for transporting a biodevice from one place to another place, comprising:
    at least one gripper mechanism for capturing the biodevice;
    a body for carrying the biodevice;
    a driving assembly for driving the body in omnidirectional motion;
    a sensing unit for sensing at least the position and orientation of the body; and
    a control unit coupled to the driving assembly and the sensing unit for generating one or more control signals based on at least the sensed position and orientation of the body to drive the driving assembly so as to move the body to a desired place and arrive with the correct orientation and direction of approach,
    wherein the at least one gripper mechanism is coupled to the body and comprises a motor and a gripper coupled to the motor such that rotation of the motor in one direction causes the gripper to retract, while the rotation of the motor in an opposite direction causes the gripper to extend so as to capture the biodevice.

2. The robot of claim 1, wherein the driving assembly comprises a plurality of movable members coupled to the body, and a plurality of drivers engaged with the plurality of movable members for operably driving the plurality of movable members individually and/or cooperatively.

3. The robot of claim 2, wherein each movable member comprises a holonomic wheel including a Mecanum wheel or an Omni wheel or a swivel drive.

4. The robot of claim 1, wherein the sensing unit is configured to sense at least the position and orientation of the body using at least one of infrared light, visible light, ultrasonic waves, and electromagnetic waves or fields.

5. The robot of claim 4, wherein the sensing unit comprises optical sensors, LiDAR sensors, accelerometers, gyroscopes, inertial measurement units (IMUs), magnetic proximity sensors, and/or pressure sensors.

6. The robot of claim 1, wherein the control unit comprises a microcontroller for operating the driving assembly and the sensing unit, and wireless communication with external devices.

7. The robot of claim 6, wherein the control unit further comprises a power supply circuit with capabilities for battery-free operation of the robot, or for battery-powered operation of the robot.

8. The robot of claim 7, wherein the power supply circuit comprises at least one battery for the battery powered operation of the robot.

9. The robot of claim 8, wherein the at least one battery is a rechargeable battery operably rechargeable with wired recharging or wireless recharging.

10. The robot of claim 1, wherein the body comprises an object handling mechanism for carrying and loading the biodevice.

11. The robot of claim 10, wherein the object handling mechanism includes the ability to raise and lower the biodevice to interface with fluid-handling, docking, and transfer stations.

12. The robot of claim 1, wherein the robot is configured to operably adjust tilt of the biodevice being carried so that the tilt compensates for an inertial force associated with acceleration and ensures that a vector sum of gravity and inertial force are always perpendicular to a bottom of the biodevice to avoid sloshing or spilling of any fluid contents of the bioobject.

13. The robot of claim 1, wherein the robot is configured to operably level the biodevice being carried as it ascends or descends a ramp between places.

14. A robotic system for fluid handling and transport of biodevices, comprising:
    a rack-type incubator having a plurality of decks, each deck having a plurality of stations, each station being configured to accommodate a perfusion module or a cell growth and plate inoculation module; and
    one or more robots, each robot being a holonomic robot configured to carry and load a biodevice to a desired module,
    wherein the rack-type incubator is configured such that two or more robots are simultaneously operable on a deck without interference.

15. The robotic system of claim 14, further comprising a means for moving a robot between decks, wherein the means comprises an elevator, or a vertical climbing shaft having climbable walls with a closeable entry door.

16. The robotic system of claim 15, wherein the robot is configured to operably climb up or down on the climbable walls, thereby moving between decks.

17. The robotic system of claim 15, further comprising an external robot arm for delivering a mobile robot or a well plate to a delivery channel of the rack-type incubator that is in communication with the elevator.

18. The robotic system of claim 14, wherein each deck is connected to a continuous circulation fluid bus and a power bus.

19. The robotic system of claim 14, wherein each robot comprises:
    a body for carrying the biodevice;

a driving assembly for driving the body in omnidirectional motion;

a sensing unit for sensing at least a position and orientation of the body; and a control unit coupled to the driving assembly and the sensing unit for generating one or more control signals based on at least the sensed position and orientation of the body to drive the driving assembly so as to move the body to a desired place and arrive with the correct orientation and direction of approach.

20. The robotic system of claim 19, wherein the driving assembly comprises a plurality of movable members coupled to the body, and a plurality of drivers engaged with the plurality of movable members for operably driving the plurality of movable members individually and/or cooperatively.

21. The robotic system of claim 20, wherein each movable member comprises a holonomic wheel including a Mecanum wheel or an Omni wheel or a swivel drive.

22. The robotic system of claim 19, wherein the sensing unit is configured to sense at least the position and orientation of the body using at least one of infrared light, visible light, ultrasonic waves, and electromagnetic waves or fields.

23. The robotic system of claim 22, wherein the sensing assembly comprises optical sensors, LiDAR sensors, accelerometers, gyroscopes, inertial measurement units (IMUs), magnetic proximity sensors, and/or pressure sensors.

24. The robotic system of claim 19, wherein the control unit comprises a microcontroller for operating the driving assembly and the sensing unit, and wireless communication with external devices.

25. The robotic system of claim 24, wherein the control unit further comprises a power supply circuit with capabilities for battery-free operation of the robot, or for battery- or supercapacitor-powered operation of the robot.

26. The robotic system of claim 19, wherein the body comprises an object handling mechanism for carrying and loading the biodevice.

27. The robotic system of claim 19, wherein the robot is configured to allow robotic exchange of one perfusion module for another.

28. The robotic system of claim 14, wherein the robotic system is configured such that an HTS Transwell plate and a well plate beneath it are separately capturable.

29. The robotic system of claim 14, wherein the biodevices comprise well plates, chemostats, organ chips, transwell-plates, or other fluidic reservoirs that are contained in a multi-element biodevice array.

30. The robotic system of claim 14, wherein the one or more robots are operable either as a single unit or in combination as a swarm.

31. The robot of claim 1, wherein the gripper has a first end pivotally coupled to the motor through a lead screw, a second end for capturing the biodevice, and a fixed pivot between the first and second ends, such that the rotation of the motor in said one direction causes the lead screw to extend, which in turn causes the first end of the gripper to move along an extended direction of the lead screw, the motion of the first end along the extended direction of the lead screw causes the second end of the gripper to retract, while the rotation of the motor in said opposite direction causes the lead screw to retract, which in turn causes the first end of the gripper to move along an retracted direction of the lead screw, the motion of the first end along the retracted direction of the lead screw causes the second end of the gripper to extend.

32. The robot of claim 1, further comprising a lift mechanism coupled with the body for raising or lowering the biodevice.

33. The robot of claim 10, wherein the object handing mechanism is configured to straddle a fixed-plate docking station to capture a bio-object for transfer.

* * * * *

UNITED STATES PATENT AND TRADEMARK OFFICE
CERTIFICATE OF CORRECTION

| | |
|---|---|
| PATENT NO. | : 11,474,531 B2 |
| APPLICATION NO. | : 17/578779 |
| DATED | : October 18, 2022 |
| INVENTOR(S) | : Ronald S. Reiserer et al. |

It is certified that error appears in the above-identified patent and that said Letters Patent is hereby corrected as shown below:

In the Specification

Column 1, Lines 18-29: reading:
"This invention was made with government support under Grant No. UH3TR002097 awarded by the National Institutes of Health (NIH) National Center for Advancing Translational Sciences (NCATS), National Institute of Neurological Disorders and Stroke (NINDS), and Eunice Kennedy Shriver National Institute of Child Health and Human Development (NICHD); Grant No. U01TR002383, and (through Vanderbilt University Medical Center) UL1TR002243 awarded by NCATS; and by the National Science Foundation (NSF) under Grant No. 2117782. The government has certain rights in the invention."

Should read as follows:
-- This invention was made with government support under Contract No. HHSN2712017000044C, and Grant Nos. TR002383, TR002243, TR002097, and CA202229, awarded by the National Institutes of Health, Grant Nos. CBET1706155 and 2117782, awarded by the National Science Foundation, and Grant No. 80NSSC20K0108, awarded by the National Aeronautics and Space Administration. The government has certain rights in the invention. --

Signed and Sealed this
Eighth Day of October, 2024

Katherine Kelly Vidal
*Director of the United States Patent and Trademark Office*